(12) United States Patent (10) Patent No.: US 9,222,882 B2
Hirabayashi et al. (45) Date of Patent: Dec. 29, 2015

(54) MEASUREMENT SYSTEM THAT ESTIMATES REFLECTION CHARACTERISTICS OF A TARGET OBJECT AND CONTROL METHOD THEREOF

(71) Applicant: CANON KABUSHIKI KAISHA, Tokyo (JP)

(72) Inventors: Jun Hirabayashi, Yokohama (JP); Takamasa Seto, Ebina (JP)

(73) Assignee: CANON KABUSHIKI KAISHA (JP)

( * ) Notice: Subject to any disclaimer, the term of this patent is extended or adjusted under 35 U.S.C. 154(b) by 0 days.

(21) Appl. No.: 14/273,766

(22) Filed: May 9, 2014

(65) Prior Publication Data

US 2014/0340707 A1 Nov. 20, 2014

(30) Foreign Application Priority Data

May 15, 2013 (JP) .................................. 2013-103536
Apr. 15, 2014 (JP) .................................. 2014-083995

(51) Int. Cl.
*G06F 3/12* (2006.01)
*G01N 21/57* (2006.01)
*H04N 1/56* (2006.01)
*G06T 15/50* (2011.01)
*H04N 1/401* (2006.01)
*G01N 21/3563* (2014.01)

(52) U.S. Cl.
CPC .............. *G01N 21/57* (2013.01); *G06F 3/1211* (2013.01); *G06F 3/1237* (2013.01); *G06T 15/506* (2013.01); *H04N 1/401* (2013.01); *H04N 1/56* (2013.01); *G01N 21/3563* (2013.01); *G06T 2200/08* (2013.01)

(58) Field of Classification Search
None
See application file for complete search history.

(56) References Cited

U.S. PATENT DOCUMENTS

| | | | |
|---|---|---|---|
| 6,733,105 B2 * | 5/2004 | Tatsumi | 347/21 |
| 2005/0168465 A1 * | 8/2005 | Tatsumi | 345/426 |
| 2010/0277477 A1 | 11/2010 | Wang et al. | |
| 2011/0032553 A1 * | 2/2011 | Funahashi | 358/1.9 |
| 2012/0045149 A1 * | 2/2012 | Arai et al. | 382/296 |
| 2012/0113307 A1 * | 5/2012 | Watanabe et al. | 348/333.01 |
| 2013/0093883 A1 * | 4/2013 | Wang et al. | 348/142 |
| 2013/0321618 A1 * | 12/2013 | Krishnaswamy et al. | 348/135 |

FOREIGN PATENT DOCUMENTS

JP 2008249521 A 10/2008

* cited by examiner

*Primary Examiner* — Miya J Cato
(74) *Attorney, Agent, or Firm* — Rossi, Kimms & McDowell LLP

(57) ABSTRACT

A measurement apparatus comprises a light source of line shape configured to move in a predetermined direction and illuminate a measurement target object, and a capturing unit configured to capture the measurement target object illuminated by the light source of line shape. The measurement apparatus controls the light source of line shape and the capturing unit, and estimates the reflection characteristics of the measurement target object from a plurality of images captured by the capturing unit.

24 Claims, 29 Drawing Sheets

F I G. 2A
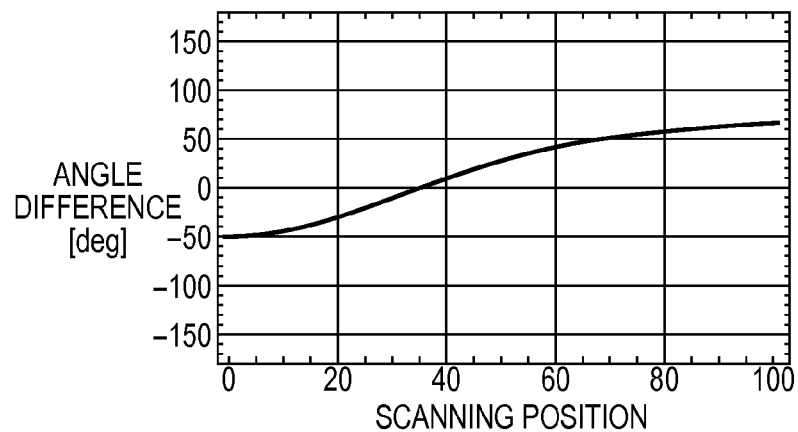
F I G. 2B
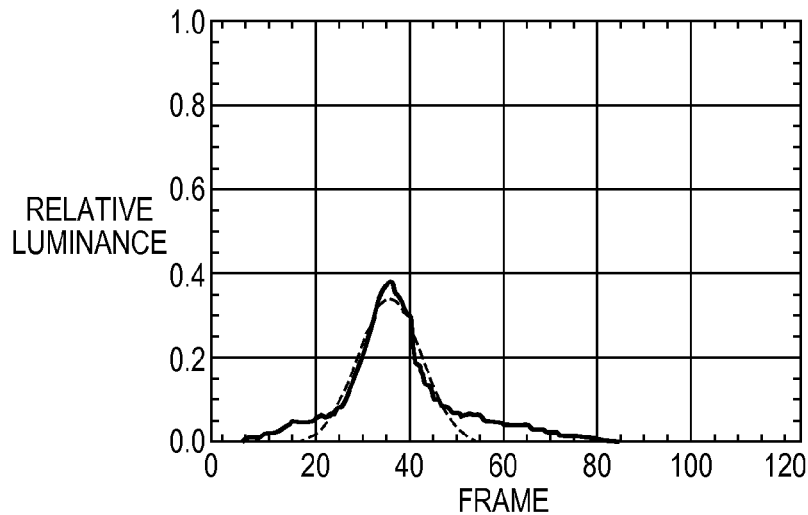
F I G. 2C
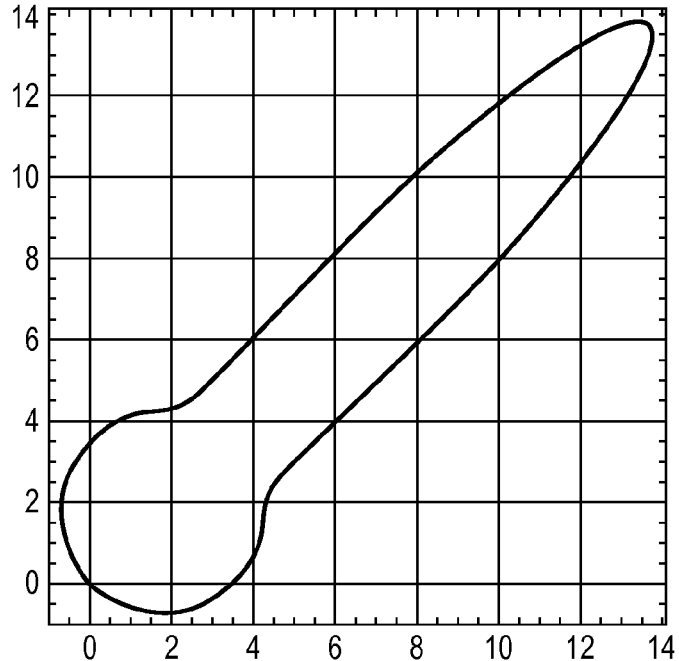

F I G. 5
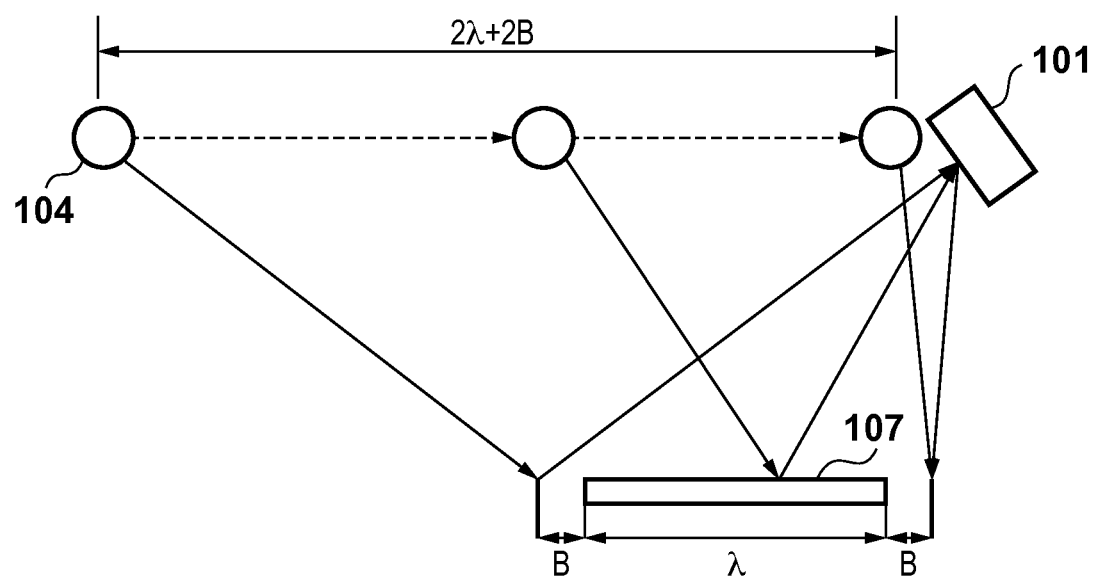

F I G. 9
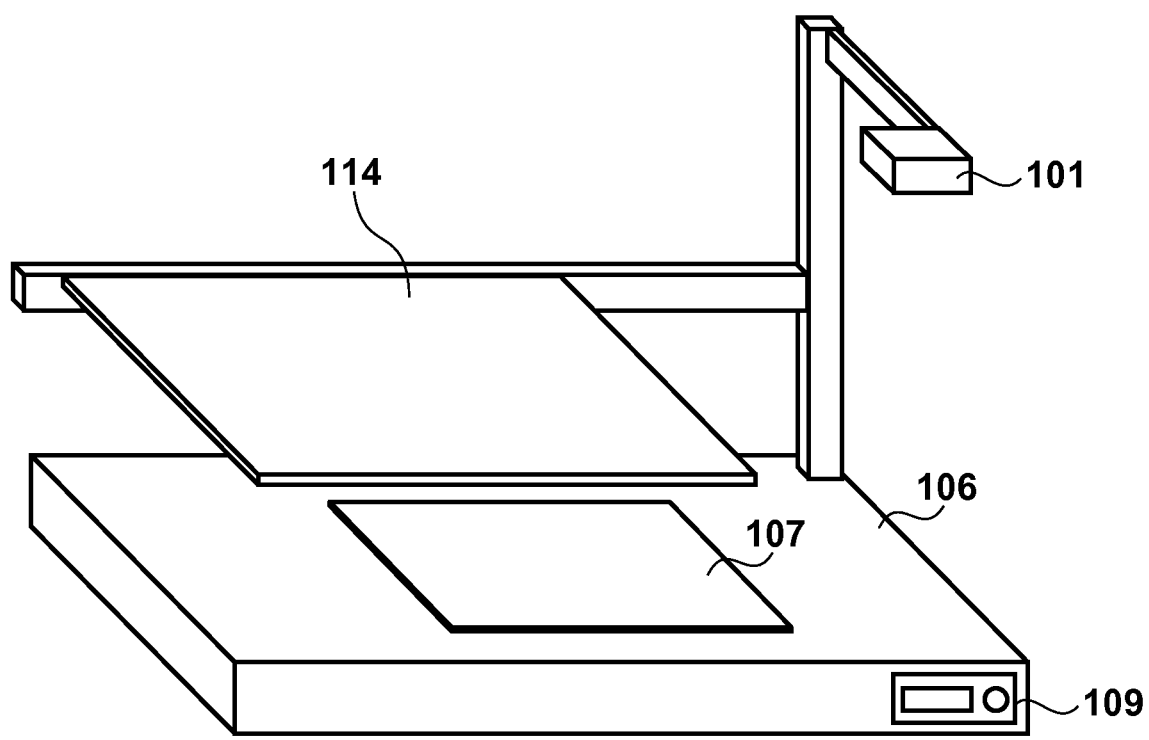

FIG. 11
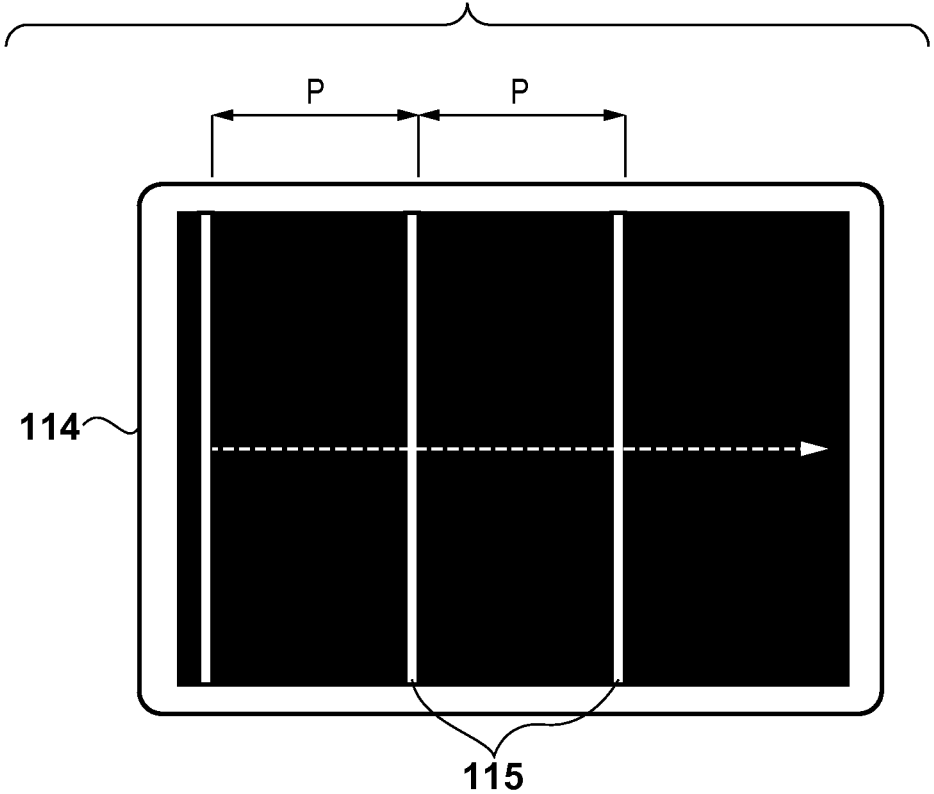
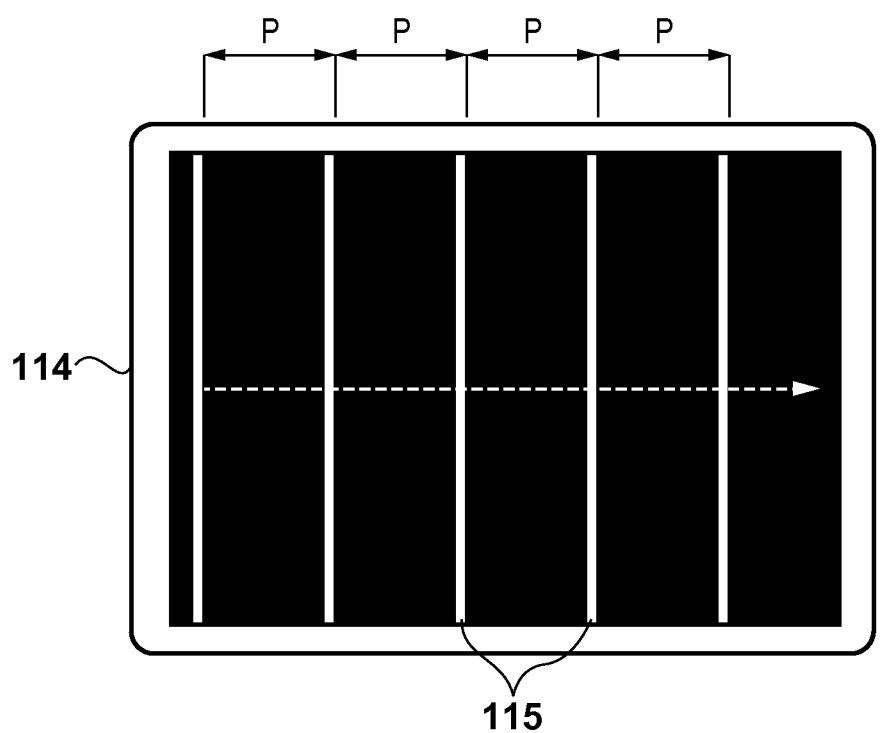

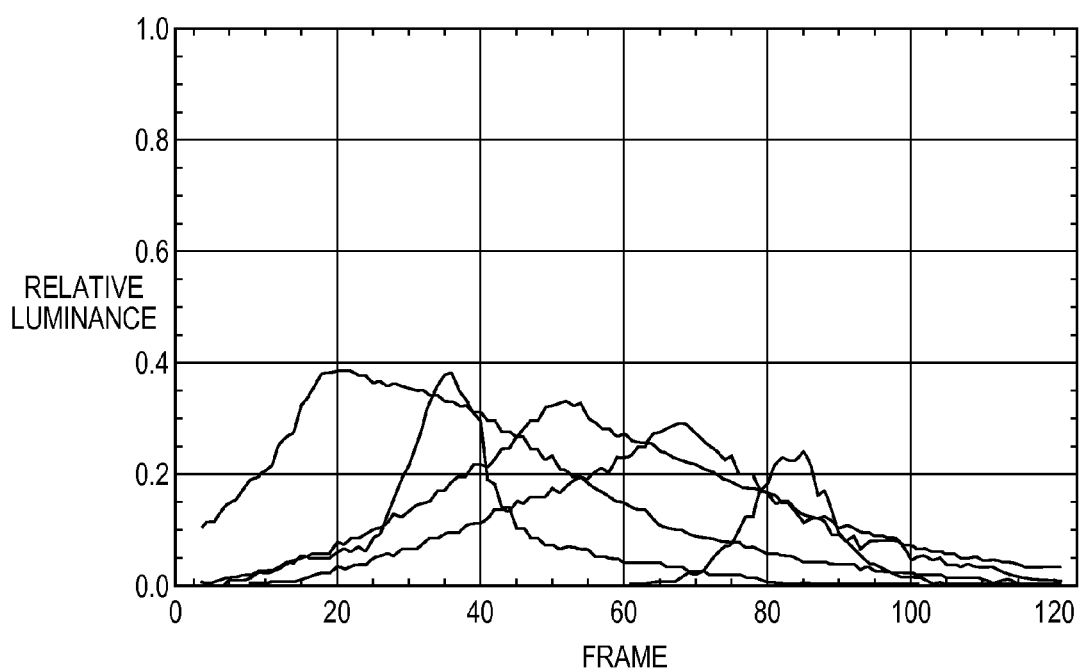
FIG. 16A
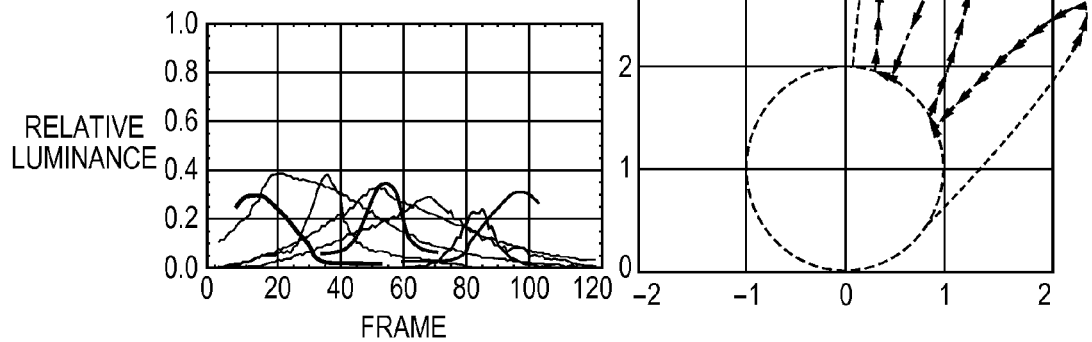
FIG. 16B
FIG. 16C

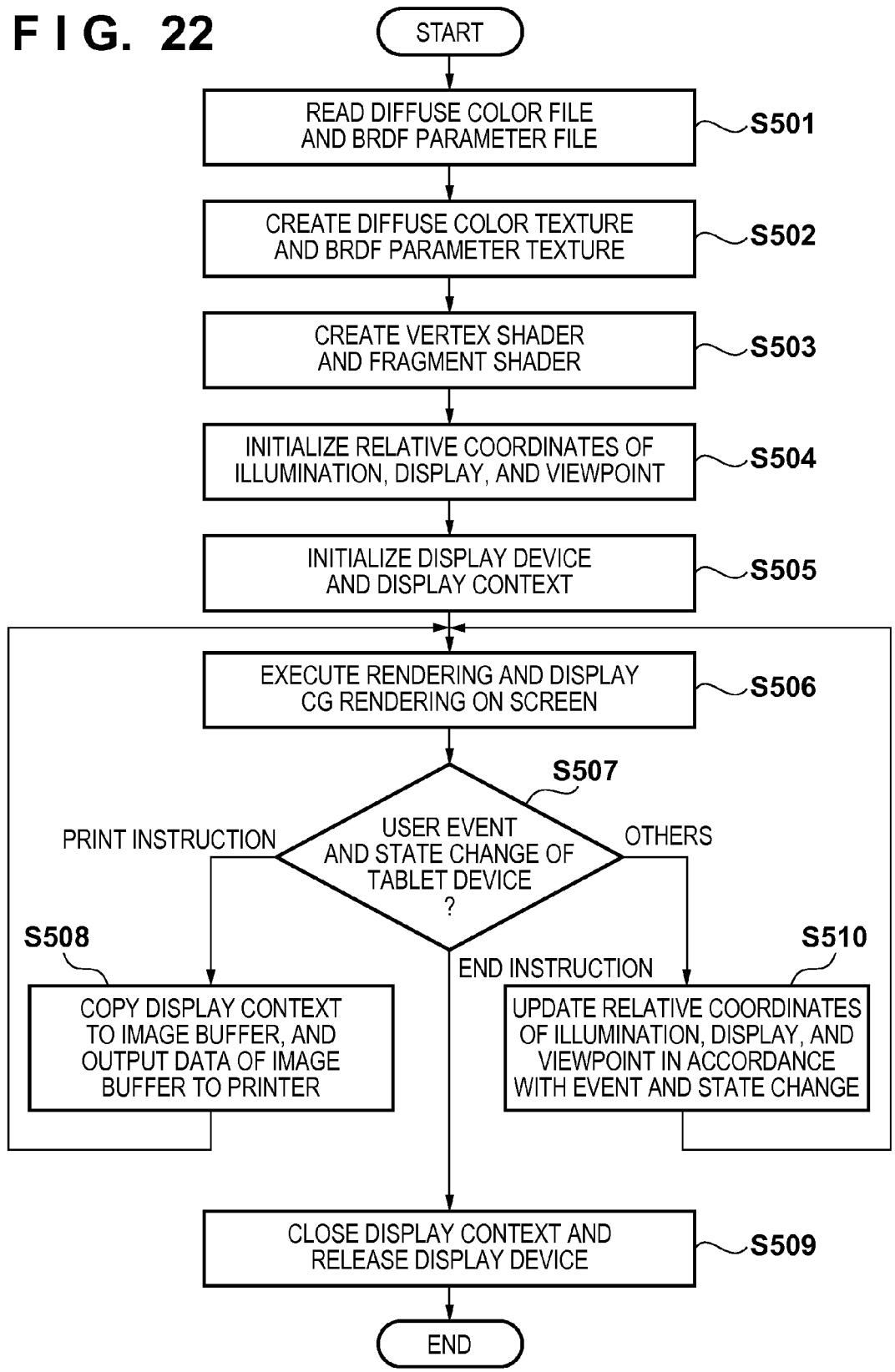

FIG. 23A  FIG. 23B  FIG. 23C
 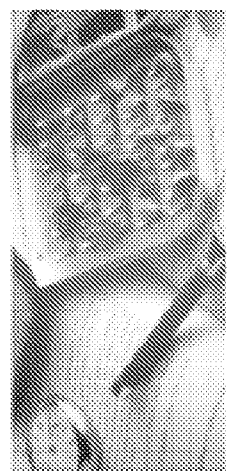 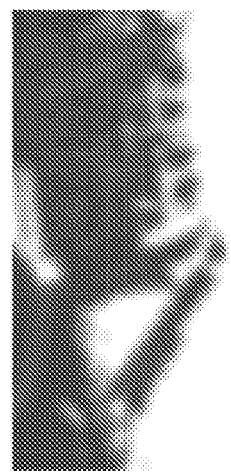
FIG. 23D  FIG. 23E  FIG. 23F
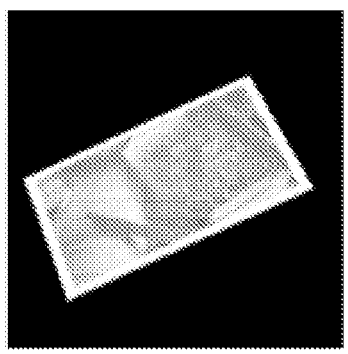 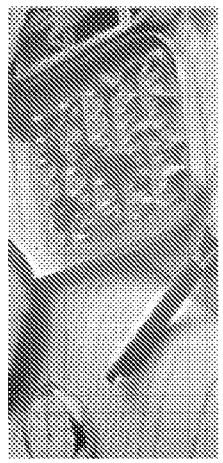 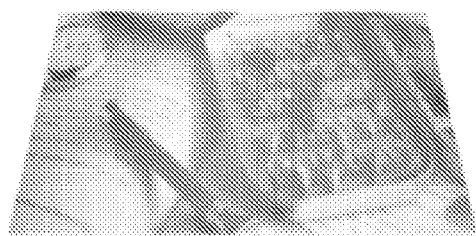

F I G. 30
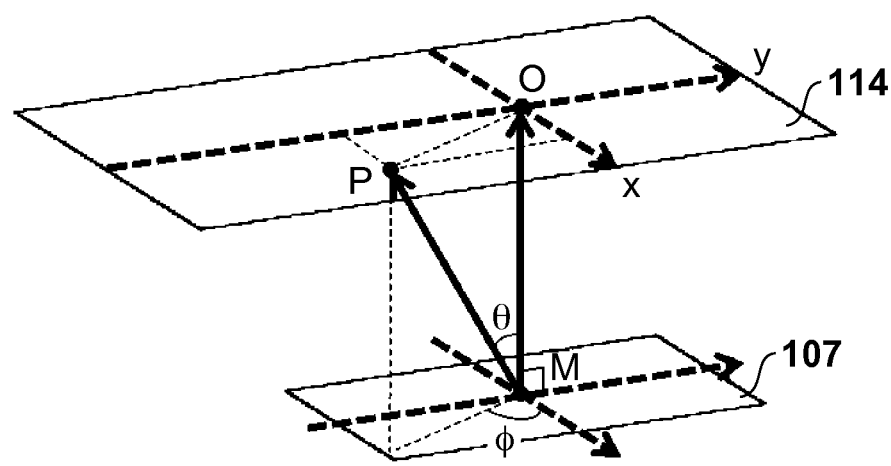
F I G. 31
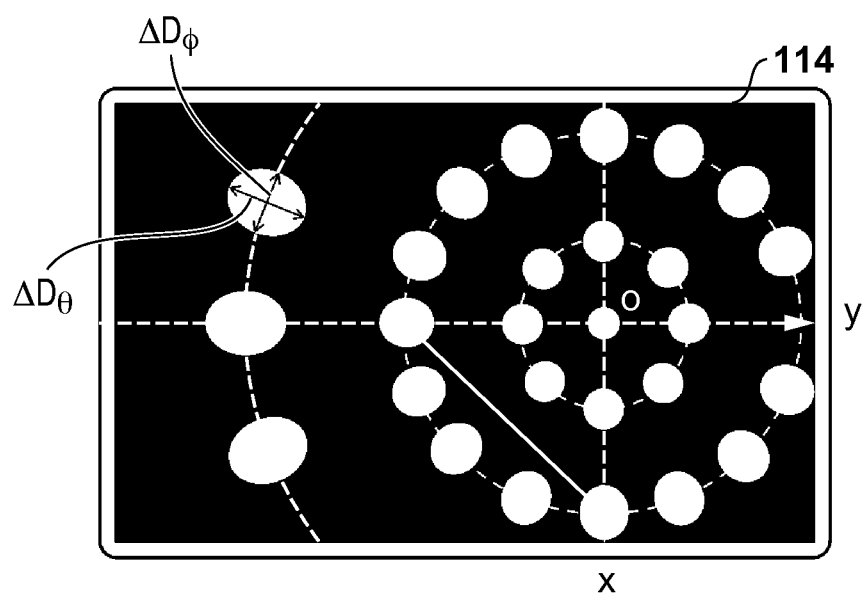

MEASUREMENT SYSTEM THAT ESTIMATES REFLECTION CHARACTERISTICS OF A TARGET OBJECT AND CONTROL METHOD THEREOF

BACKGROUND OF THE INVENTION

1. Field of the Invention

The present invention relates to measurement of the optical characteristics of an object.

2. Description of the Related Art

The color and gloss of an object are represented by diffuse light (color) colored in a coating film on the surface of the object or inside the object, and specular reflection light (color) of illumination light reflected by the coating film or the object surface. As for the surface of a printed material, diffuse light exhibits relatively the same isotropy when viewed from any direction. To the contrary, reflected light changes depending on the incident direction (illumination direction) of illumination light with respect to the surface of a printed material, and the exit direction (observation direction) of the reflected light.

To obtain the characteristic of the color (and gloss) of an object in an arbitrary illumination direction and observation direction, the object is irradiated with illumination light from various directions to measure light (color) radiating from the surface of the object omnidirectionally to the periphery of the object. The measurement result is called a bidirectional reflectance distribution function (BRDF). As the radiation distribution characteristic of reflected light from an object to the periphery, the BRDF is used in various applications such as computer graphics (CG).

There is known the first technique of acquiring the BRDF of an object by radiating light at an arbitrary portion on a hemispherical surface around the object and receiving it at an arbitrary portion on the hemispherical surface. According to the first technique, the BRDF of an object can be acquired. However, the BRDF obtained by one measurement is merely the measurement result of one point on the reflecting surface of the object. A very long measurement time is required to measure an object whose BRDF changes depending on the location.

There is also known the second technique of acquiring BRDFs from a plurality of two-dimensional images obtained by scanning a measurement target surface with a light source of line shape and capturing reflected light beams at respective scanning positions with a camera. According to the second technique, the BRDFs of respective points on a measurement target surface can be measured by one scanning and a plurality of image capturing operations.

When only the color of a measurement target surface, that is, the color of diffuse light (to be referred to as "diffuse color" hereinafter) is acquired, measurement ends by only one capturing if a two-dimensional image sensor (for example, a camera apparatus) is used. Even when the color is acquired by a line sensor (for example, a scanner apparatus), measurement ends by a line sensor scanning length equal to the length of the measurement target surface. However, even if the second technique is employed, the acquisition of the BRDF requires a much longer measurement time, compared to the acquisition of only the color (diffuse color), because the scanning length of the light source of line shape becomes double or larger than the length of the measurement target surface.

SUMMARY OF THE INVENTION

In an aspect, a measurement apparatus comprising: a light source of line shape configured to move in a predetermined direction and illuminate a measurement target object; a capturing unit configured to capture the measurement target object illuminated by the light source; a control unit configured to control the light source and the capturing unit; and an estimation unit configured to estimate reflection characteristics of the measurement target object from a plurality of images captured by the capturing unit.

According to the aspect, the optical characteristics of an object can be measured in a short time.

Further features of the present invention will become apparent from the following description of exemplary embodiments with reference to the attached drawings.

BRIEF DESCRIPTION OF THE DRAWINGS

FIGS. 2A to 2C are graphs respectively showing the relationship between the scanning position and specular reflection, an example of luminance transition, and an example of the BRDF.

FIG. 5 is a view showing a scanning range necessary for a line light source.

FIG. 9 is a view showing an outline of a measurement apparatus according to the second embodiment.

FIG. 11 is a view showing a display example of a display.

FIGS. 16A to 16C are graphs showing a luminance change of pixels corresponding to several points on the reflecting surface of the measurement target object.

FIGS. 18A to 18C are views showing an example of CG rendering using a measured BRDF distribution.

FIG. 22 is a flowchart for explaining an example of CG rendering preview processing.

FIGS. 23A to 23F are views respectively showing a measurement target object, a diffuse color distribution, a BRDF distribution, a preview screen, a state in which CL data overlaps a diffuse color texture, and a printing result in which a transparent color material overlaps a printed image of the diffuse color texture based on the CL data.

FIG. 30 is a view illustrating the geometric condition of the display and reflecting surface.

FIG. 31 is a view illustrating the emission pattern of the display.

DESCRIPTION OF THE EMBODIMENTS

Measurement of the optical characteristics of an object according to embodiments of the present invention will now be described in detail with reference to the accompanying drawings.

First Embodiment

Outline of Apparatus

Figure 1:
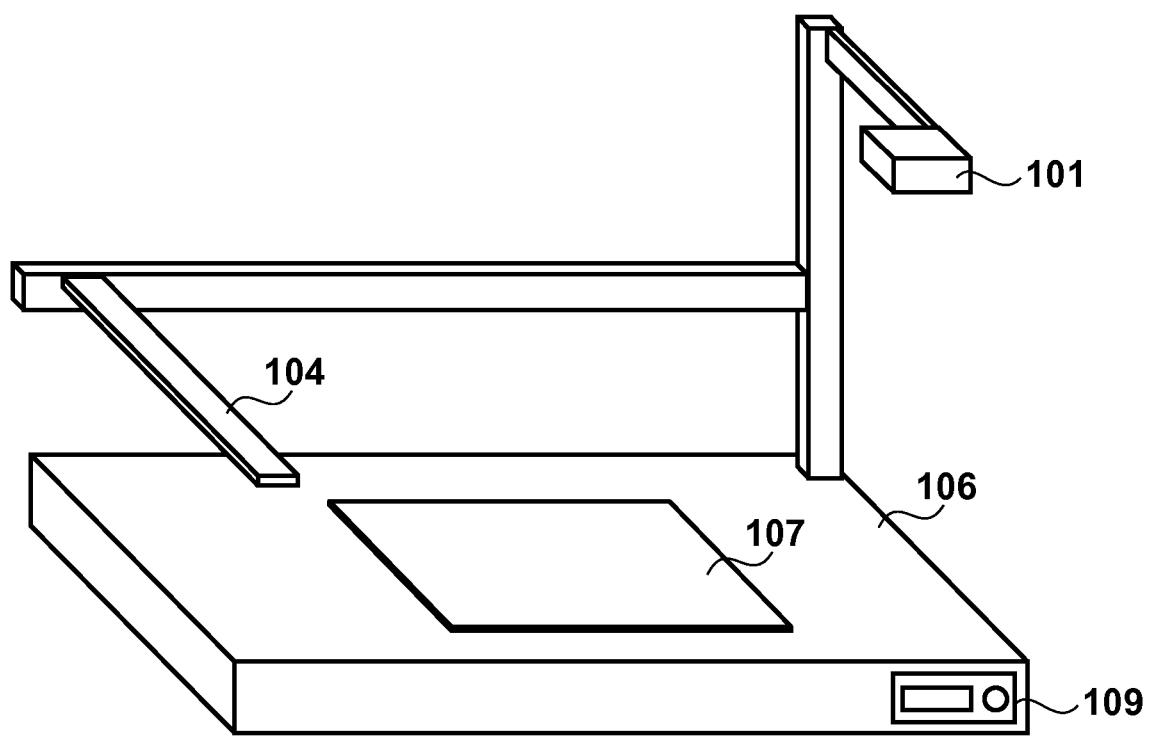
FIG. 1 is a view showing an outline of a measurement apparatus according to the first embodiment.

FIG. 1 shows an outline of a measurement apparatus according to the first embodiment.

In the measurement apparatus, a movable light source 104 of line shape (to be referred to as a "line light source" hereinafter) illuminates the reflecting surface of a measurement target object 107 (sometimes simply called a "reflecting surface") set on a measurement table 106. A capturing unit (camera) 101 including a two-dimensional image sensor captures, as an image, the light reflected by the reflecting surface, measuring the distribution of the gloss characteristic (bidirectional reflectance distribution function (BRDF) or glossiness) of the reflecting surface, which is the reflection characteristic of the measurement target object 107. The scanning condition (moving position) of the line light source 104 is controlled in accordance with information representing the size of the reflecting surface and the material of the object, details of which will be described later.

More specifically, the line light source 104 is positioned by a predetermined distance above the measurement target object 107, and moves in a predetermined direction while irradiating the measurement target object 107 with light. The camera 101 arranged at a predetermined position above the measurement target object 107 sequentially captures the specular reflection light and diffuse color from the measurement target object 107. The captured image is used in BRDF estimation, details of which will be described later. The moving range of the line light source 104 will also be described later.

By the movement, that is, scanning of the line light source 104, the incident angle of light from the line light source 104 with respect to each small region of the reflecting surface changes. The positional relationship between the reflecting surface and the camera 101 is fixed, and an angle (to be referred to as a "line-of-sight angle" hereinafter) defined by the normal of each small region of the reflecting surface and the normal of the two-dimensional image sensor of the camera 101 is fixed for each small region. Along with scanning of the line light source 104, light from the line light source 104 is specularly reflected in a small region where (the absolute values of) the incident angle of light and the line-of-sight angle are equal to each other. The light reaches the two-dimensional image sensor and is captured as an image.

FIG. 2A shows the relationship between the scanning position and specular reflection. In FIG. 2A, the abscissa represents the scanning position of the line light source 104, and the ordinate represents the difference (angle difference) between an incident angle (absolute value) with respect to a region R1 on the measurement target object 107, and the angle (absolute value) of a line segment connecting the region R1 and a region R2 on the two-dimensional image sensor. On the ordinate, an angle difference of 0 is the condition of specular reflection. A negative angle difference indicates that the incident angle is smaller than an angle at which specular reflection occurs, and a positive angle difference indicates that the incident angle is larger than the angle at which specular reflection occurs. That is, the positional relationship between the regions R1 and R2 satisfies the condition of specular reflection by scanning the line light source 104, and then deviates from it.

Figure 3B:
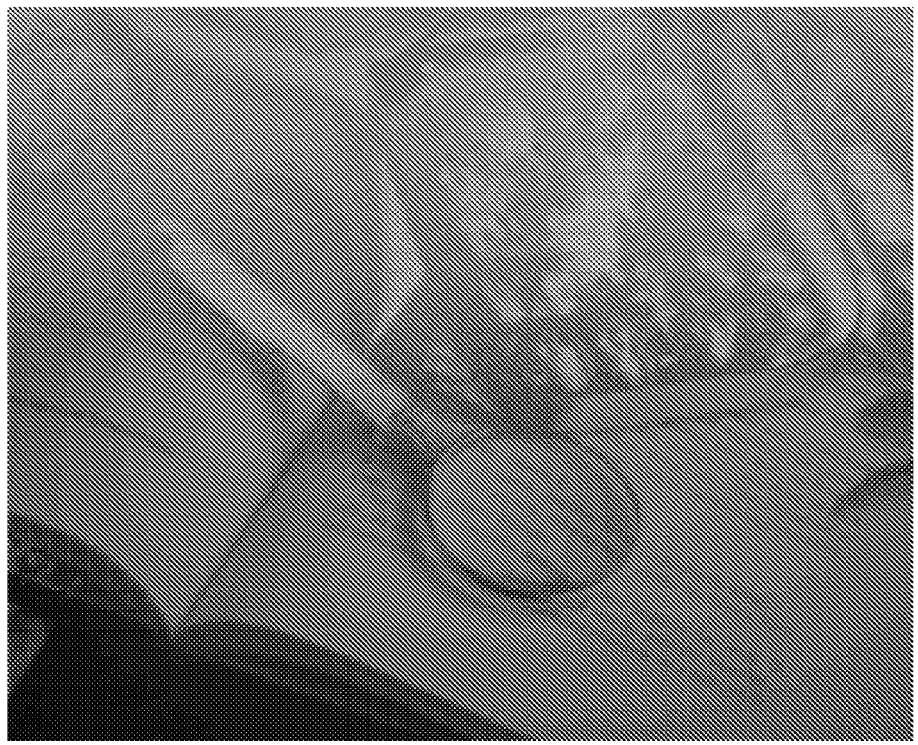
FIGS. 3A and 3B are views respectively showing an example of an image (read image) obtained by compositing a plurality of captured images, and an example of CG rendering using a BRDF distribution on a reflecting surface.
Figure 3A:
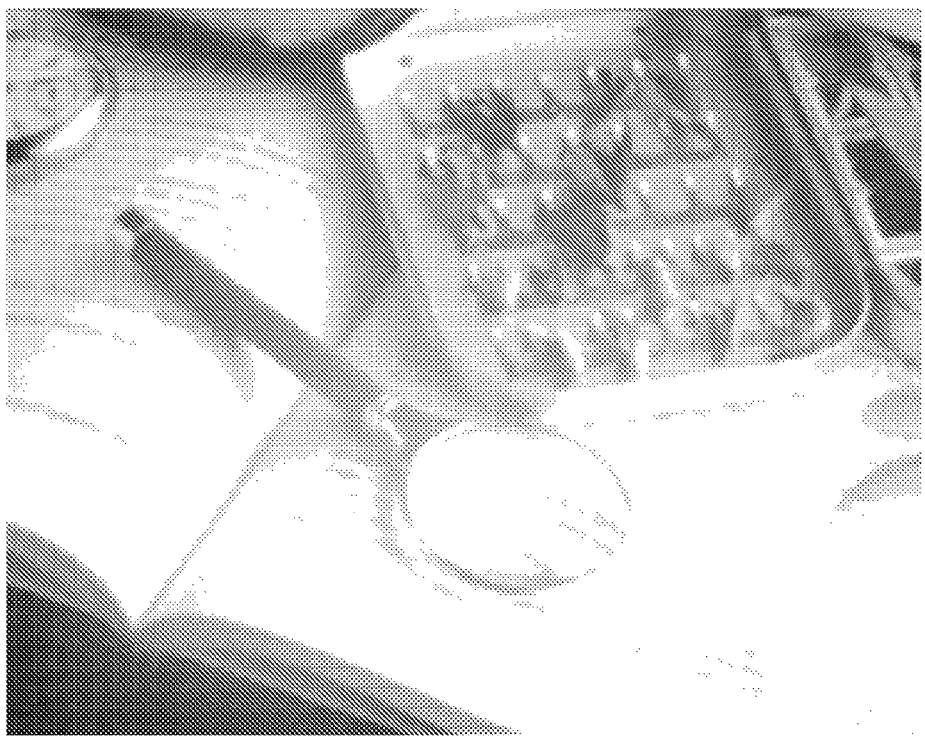

FIG. 3A shows an example of an image (read image) obtained by compositing a plurality of captured images. Each image captured by the camera 101 is an image formed on the reflecting surface while the line light pattern of the line light source 104 moves on the reflecting surface. A plurality of captured images (to be referred to as an "image group" hereinafter) are composited, obtaining a read image.

[Apparatus Arrangement]

Figure 4:
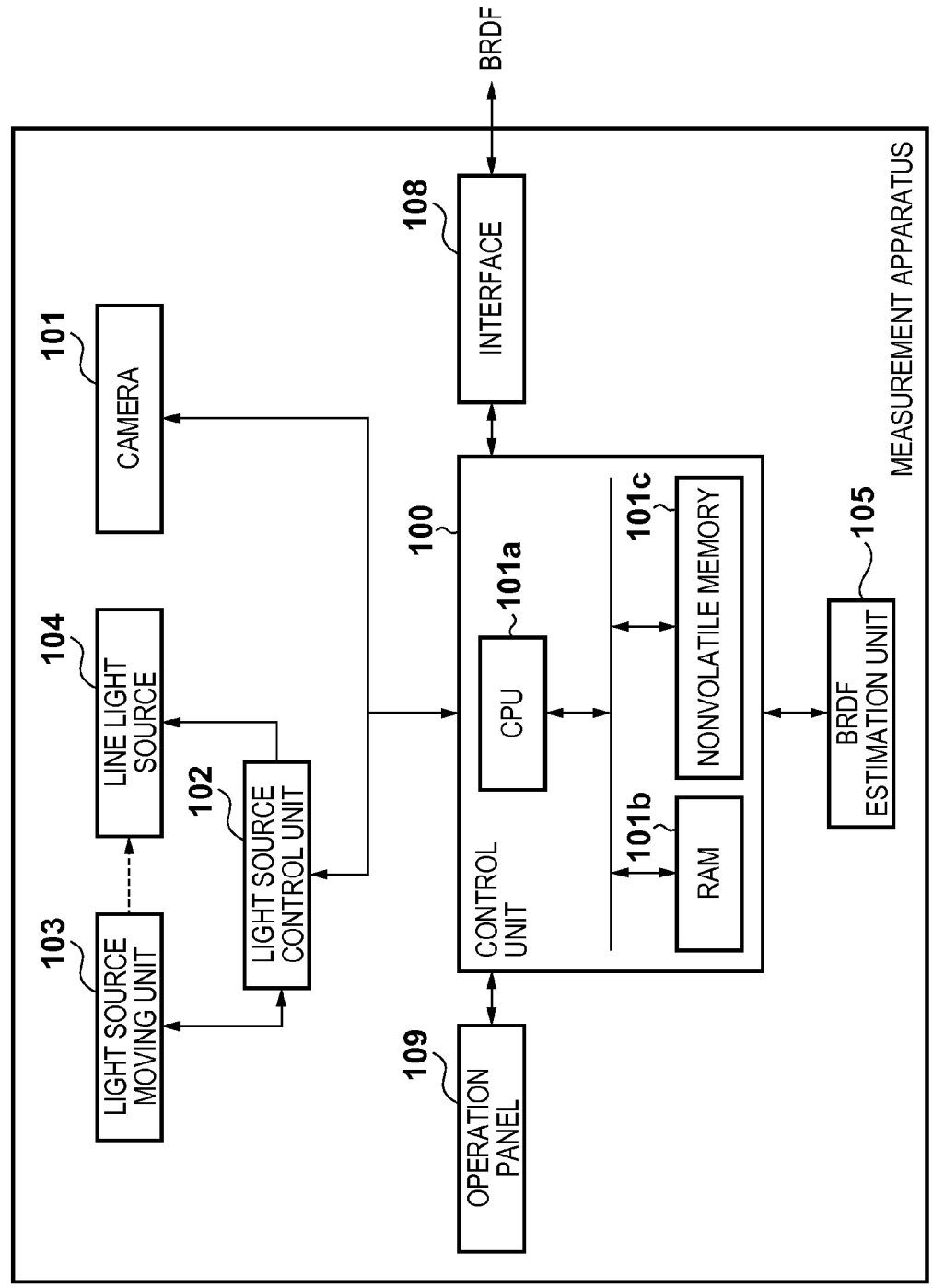
FIG. 4 is a block diagram showing the arrangement of the measurement apparatus.

The arrangement of the measurement apparatus is shown in the block diagram of FIG. 4. By using a random access memory (RAM) 100b as a work memory, a control unit 100 including a microprocessor (CPU) 100a executes a program stored in a nonvolatile memory 100c such as a read only memory (ROM) or flash memory, and controls an arrangement to be described below.

In accordance with an instruction from the control unit 100, a light source control unit 102 controls the ON/OFF operation of the line light source 104, and the operation of a light source moving unit 103 for moving the line light source 104. Based on a signal output from the light source moving unit 103, the light source control unit 102 outputs, to the control unit 100, a scanning position signal representing the scanning position of the line light source 104.

When the measurement start button of an operation panel 109 is pressed or a measurement start instruction is received from a computer device connected to an interface 108, the control unit 100 instructs the light source control unit 102 to turn on and move the line light source 104. Based on a scanning position signal input from the light source control unit 102, the control unit 100 controls capturing of the camera 101, and stores image data output from the camera 101 in a memory such as the RAM 100b or a hard disk drive (HDD).

Upon receiving a signal representing the end of scanning of the line light source 104 from the control unit 100, a BRDF estimation unit 105 calculates or estimates the BRDF of the measurement target object 107 from image data of the image group stored in the memory. After the end of calculating or estimating the BRDF by the BRDF estimation unit 105, the control unit 100 outputs the calculated or estimated BRDF thorough the interface 108. The BRDF output destination is arbitrary and is, for example, a recording medium (for example, a USB (Universal Serial Bus) memory) or a computer apparatus connected to the interface 108, or a computer apparatus or server apparatus on a network connected through the interface 108.

Calculation of BRDF

In general, a BRDF model represents a BRDF as the sum of the diffuse component and specular reflection component. That is, the BRDF is often represented as:

$$I\text{reflection} = I\text{specular} + I\text{diffusion} \quad (1)$$

where

Ireflection: intensity of reflected light

Ispecular: intensity of the specular reflection light component

Idiffusion: intensity of the diffuse reflection light component

For example, a Cook-Torrance (Torrance-Sparrow) model represents the intensity Ispecular of the specular reflection light component in equation (1) by using several parameters:

$$I\text{specular} = I\text{light}(F[\ ]/\pi)\{D[\ ]G[\ ]/(\vec{N}\cdot\vec{V})\} \quad (2)$$

where

Ilight: intensity of incident light

F[ ]: Fresnel reflection coefficient (equation (3)) representing a change of the reflection coefficient depending on the reflection angle D[ ]: microscopic normal distribution (equation (4)) of the reflecting surface represented by a Bechmann distribution function using a micro facets coefficient G[ ]: geometric attenuation coefficient (equation (5)) representing mask shadowing based on microscopic irregularities calculated using D[ ]

$\vec{N}$: normal vector of the reflecting surface $\vec{V}$: line-of-sight direction vector representing the direction of the camera 101 from a point on the reflecting surface Fresnel reflection coefficient F[ ]:

$$F[\ ] = (Fp^2 + Fs^2)/2 \quad (3)$$

where $Fp = [\cos\theta - \sqrt{\{n^2 - (\sin\theta)^2\}}]/[\cos\theta + \sqrt{\{n^2 - (\sin\theta)^2\}}]$
$Fs = [n^2 \cos\theta - \sqrt{\{n^2 - (\sin\theta)^2\}}]/[\cos\theta + \sqrt{\{n^2 - (\sin\theta)^2\}}]$
$\theta$: incident angle
n: refractive index of the reflecting surface Microscopic normal distribution D[ ]:

$$D[\ ] = \{1/(4m^2 \cos^4\alpha)\}\exp\{-(\tan\alpha/m)^2\} \quad (4)$$

where m: roughness of the reflecting surface (micro facets coefficient)

$\alpha$: angle between the half-angle vector $\vec{H}$ and the normal vector $\vec{N}$ $\vec{H}$: vector (half-angle vector) facing the middle between the light source direction vector $\vec{L}$ and the line-of-sight direction vector $\vec{V}$ Geometric attenuation coefficient G[ ]:

$$G[\ ] = \min[1, \{2(\vec{N}\cdot\vec{H})(\vec{N}\cdot\vec{V})/(\vec{V}\cdot\vec{H})\}, \{2(\vec{N}\cdot\vec{H})(\vec{N}\cdot\vec{L})/(\vec{V}\cdot\vec{H})\}] \quad (5)$$

where min( ): function of giving a minimum value

In these equations, unknown parameters are the micro facets coefficient m which is constant in each small region, and the refractive index n of the reflecting surface. When the measurement target object 107 is a printed material, the refractive index n of a generally used color material (for example, ink or toner) is about 1.6, and unknown parameters (in, for example, the Cook-Torrance model) can be simplified into only the micro facets coefficient m.

For this reason, the micro facets coefficient m in each region of the reflecting surface is calculated from a plurality of reflected light amount conditions corresponding to different incident angles in capturing by the camera 101 when the line light source 104 moves. As a result, the reflected light characteristic distribution (BRDF distribution) of the reflecting surface can be acquired.

For example, FIG. 2B shows the transition of the luminance at a given point on the reflecting surface that is acquired from a plurality of images captured while moving the line light source 104. A peak near frame number 35 indicates the specular reflection light component. From the peak of the luminance transition, the BRDF estimation unit 105 calculates the micro facets coefficient ma of the Cook-Torrance model (to minimize a mean square error). Further, a Lambert reflection model, in which the average value of a region excluding the peak of the luminance transition is used as a diffuse color component and the diffuse color component is set as a maximum value, is used for the diffuse color component of the BRDF. By this processing, an example (specular reflection light component·diffuse color component) of the BRDF shown in FIG. 2C is obtained with respect to the example of the luminance transition in FIG. 2B.

Here, the example using the Cook-Torrance (Torrance-Sparrow) model as a model representing the specular reflection light component of the BRDF has been explained. However, even if another BRDF model is used, the parameters of the BRDF model can be calculated from a plurality of captured images along with scanning of the line light source 104, as in the above-described mode, as long as the model is represented by several parameters.

FIG. 3B shows an example of CG rendering using the BRDF distribution of the reflecting surface. The BRDF distribution of the reflecting surface can be used in various applications. For example, by performing CG rendering, the reflecting surface can be reproduced on the display. In the example of FIG. 3B, the appearance of the reflecting surface corresponding to the light source position (direction) and viewpoint position (direction) is reproduced.

[Scanning of Line Light Source]

To acquire the BRDF distribution of the reflecting surface, the line light source 104 needs to scan at least a position (to be referred to as a "specular reflection position" hereinafter) at which light emitted by the line light source 104 and specularly reflected by the reflecting surface enters the camera 101. Further, unless the transition of the tail of the peak of the luminance transition described above is acquired, the estimation accuracy of the BRDF parameter representing the specular reflection light component drops. To prevent this, it is insufficient that the line light source 104 only passes the specular reflection position. The line light source 104 needs to be scanned by a width by which the tail can be satisfactorily captured, in other words, positions preceding and succeeding the specular reflection position (from a position at which the specular reflection light component is sufficiently small, to a position at which the specular reflection light component becomes sufficiently small, across the peak).

FIG. 5 shows a scanning range necessary for the line light source 104. Letting λ be the length of the measurement target object 107 in the scanning direction of the line light source 104, and B be the spread amount of the specular reflection light component, the scanning length of the line light source 104 is at least 2λ+2B. The line light source 104 is scanned generally at a constant speed, and the scanning time is proportional to the scanning length.

In the embodiment, minimum scanning is performed by controlling the scanning length of the line light source 104 in accordance with conditions such as the size, type (paper type or material), and rough gloss information (visual perception of the material) of the measurement target object 107 (or reflecting surface). This minimizes the time to acquire the BRDF distribution of the reflecting surface.

Figure 6:
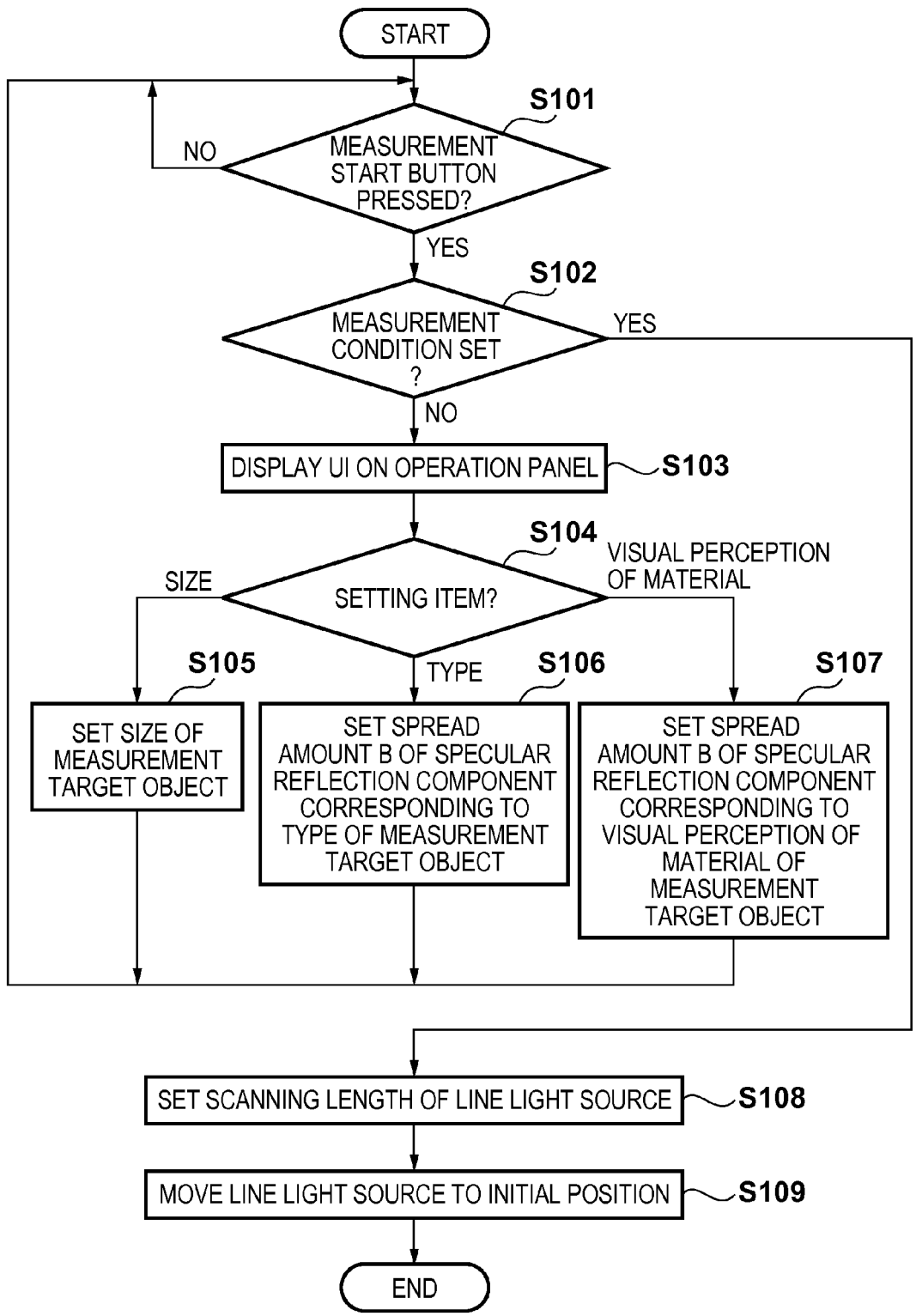
FIG. 6 is a flowchart for explaining initial setting processing for a line light source.

Initial setting processing for the line light source 104 will be explained with reference to the flowchart of FIG. 6.

The control unit 100 determines whether the measurement start button has been pressed (S101). If the measurement start button has been pressed, the control unit 100 determines whether the length λ of the measurement target object 107 and the spread amount B (measurement condition) of the specular reflection light component have been set (S102). If a measurement condition has been set, for example, if a measurement condition has been set from an external computer device, the control unit 100 sets the scanning length 2λ+2B of the line light source 104 (S108), and moves the line light source 104 to an initial position (S109).

If at least either of the length λ and spread amount B has not been set, the control unit 100 displays a user interface (UI) representing setting items on, for example, the operation panel 109 (S103), and waits for selection of a setting item by the user (S104). If the user selects the size of the measurement target object 107 (or reflecting surface) as a setting item, the control unit 100 sets, as the length λ, a numerical value input to a displayed UI for inputting the length λ (S105), and then returns the process to step S101.

If the user selects the type of the measurement target object 107 as a setting item, the control unit 100 sets the spread amount B of the specular reflection light component corresponding to a type input to a displayed UI for inputting the type (S106), and then returns the process to step S101. If the user selects the visual perception of the material of the measurement target object 107 as a setting item, the control unit 100 sets the spread amount B of the specular reflection light component corresponding to a visual perception of the material input to a displayed UI for inputting the visual perception of the material (S107), and then returns the process to step S101.

[Acquisition of BRDF Distribution]

Figure 7:
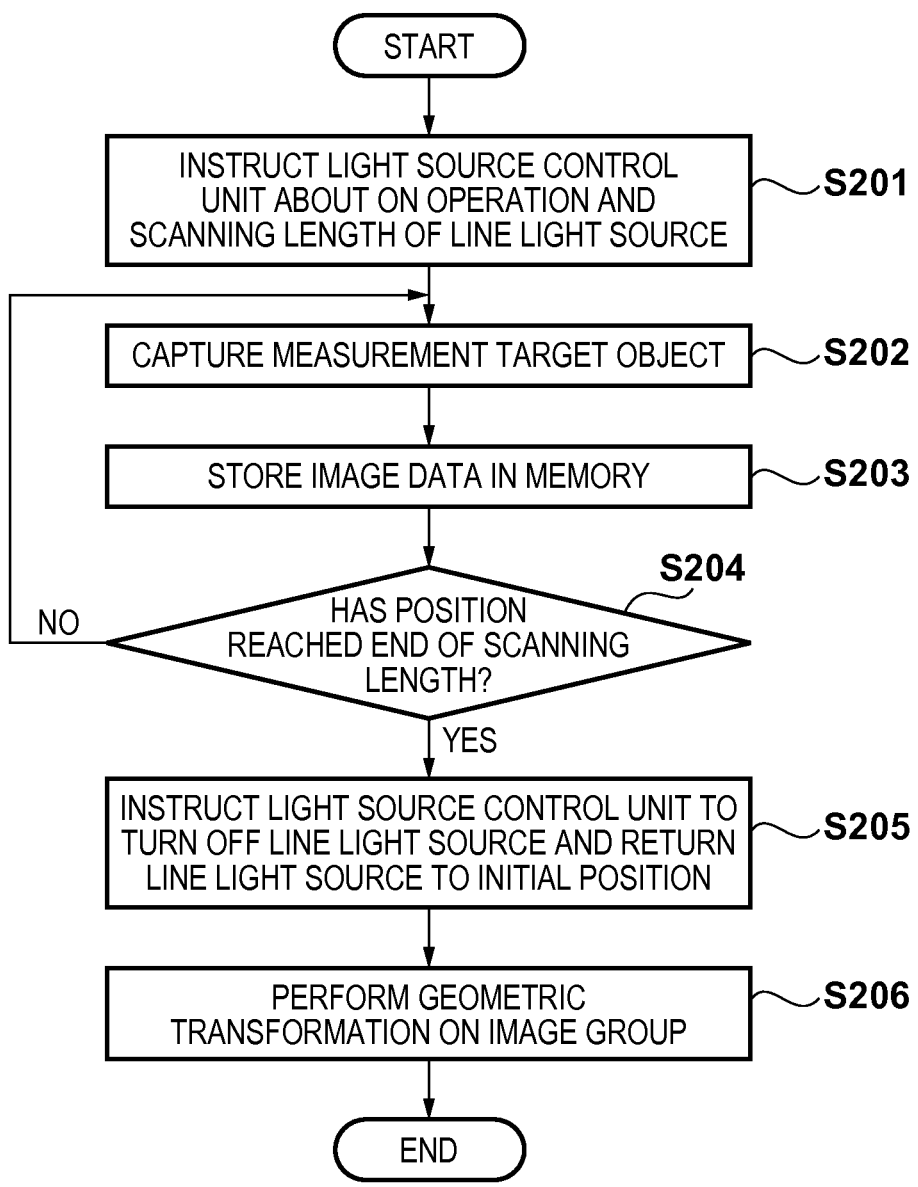
FIG. 7 is a flowchart for explaining capturing processing for a measurement target object.

Capturing processing for the measurement target object 107 will be explained with reference to the flowchart of FIG. 7. Note that the capturing processing is executed after the initial setting processing shown in FIG. 6.

The control unit 100 instructs the light source control unit 102 about the ON operation and scanning length of the line light source 104 (S201). In accordance with this instruction, the light source control unit 102 turns on the line light source 104 and starts moving the line light source 104.

Based on a scanning position signal input from the light source control unit 102, the control unit 100 controls the camera 101 to capture the measurement target object 107 (S202). The control unit 100 stores image data output from the camera 101 in the memory (for example, the RAM 100b) (S203). The control unit 100 determines whether the position indicated by the scanning position signal has reached the end of the scanning length (S204). If the position has not reached the end, the control unit 100 returns the process to step S202 to continue capturing.

If the position indicated by the scanning position signal has reached the end of the scanning length, the control unit 100 instructs the light source control unit 102 to turn off the line light source 104 and return the line light source 104 to the initial position (S205). In accordance with this instruction, the light source control unit 102 turns off the line light source 104 and returns the line light source 104 to the initial position.

After that, the control unit 100 performs geometric transformation on the image group stored in the memory to exclude the influence of the projection angle of the camera 101 (S206), and ends the capturing processing.

Figure 8:
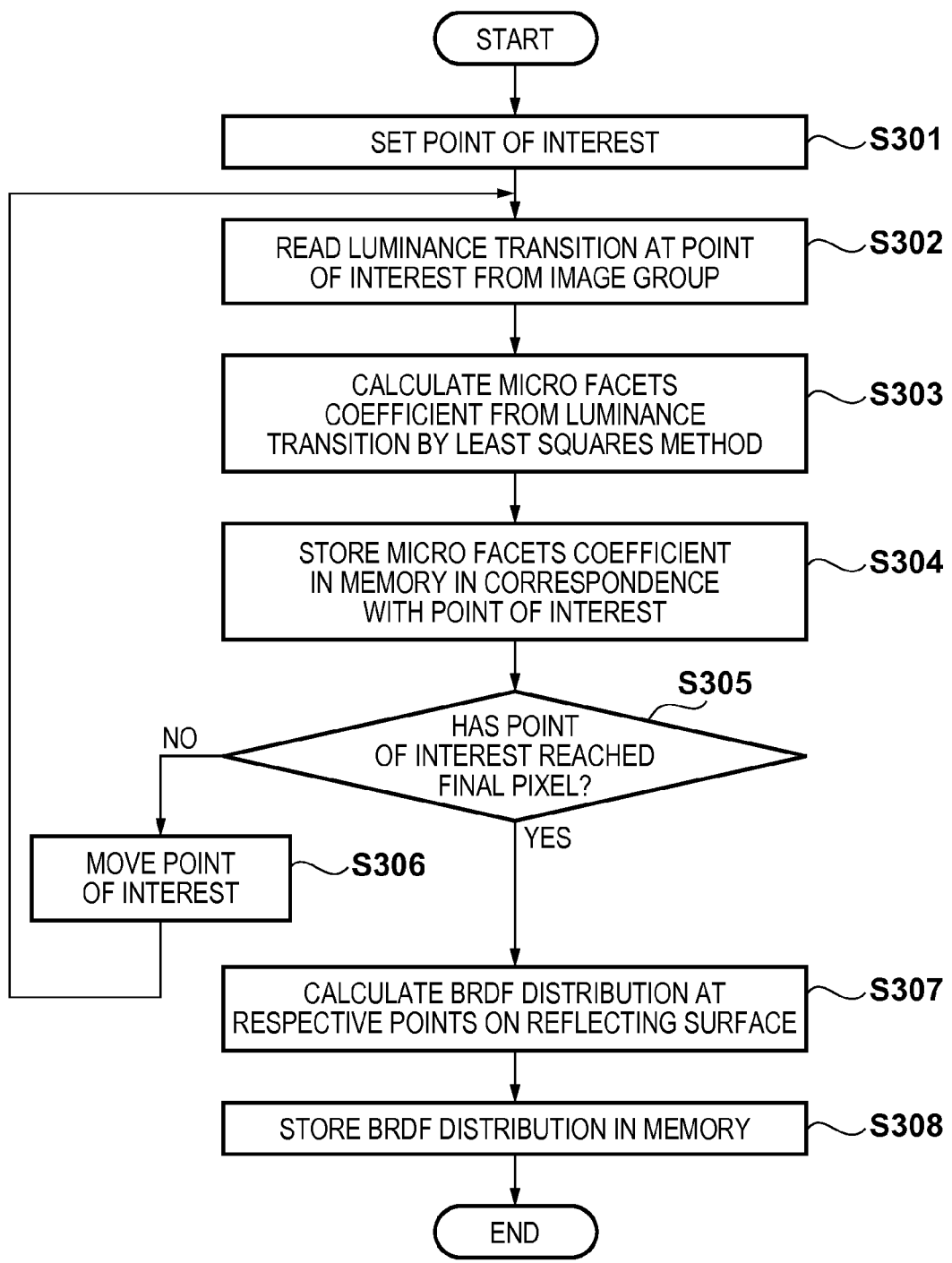
FIG. 8 is a flowchart for explaining BRDF distribution calculation processing.

BRDF distribution calculation processing will be described with reference to the flowchart of FIG. 8.

After the end of capturing processing, the BRDF estimation unit 105 executes BRDF distribution calculation processing by referring to image data of the image group which has undergone geometric transformation and has been stored in the memory.

The BRDF estimation unit 105 sets the origin (for example, an upper left pixel) of the image as a point of interest (S301), and then reads the luminance transition at the point of interest from the image group (S302). The BRDF estimation unit 105 calculates the micro facets coefficient m from the luminance transition by the least squares method (S303), and stores the calculated micro facets coefficient m in the memory (for example, the RAM 100b) in correspondence with the point of interest (S304).

Then, the BRDF estimation unit 105 determines whether the point of interest has reached the final pixel (for example, a lower right pixel) (S305). If the point of interest has reached the final pixel, the BRDF estimation unit 105 ends the process. If the point of interest has not reached the final pixel, the BRDF estimation unit 105 moves the point of interest in the raster order (S306), and returns the process to step S302. The BRDF estimation unit 105 repeats the processes in steps S302 to S305 until the micro facets coefficients m corresponding to all the pixels of the image are calculated.

Then, the BRDF estimation unit 105 calculates the BRDF distribution at respective points on the reflecting surface that correspond to respective pixels by using the calculated micro facets coefficients m and equations (1) to (5) (S307). The BRDF estimation unit 105 stores the calculated BRDF distribution in the memory (for example, the RAM 100b) (S308), and ends the process.

Calculation of Micro Facets Coefficient m

Assume that the camera 101 and the reflecting surface of the measurement target object 107 are arranged at a distance determined in advance from the structure, or a distance which can be obtained in advance from the focus position of the camera 101. Also, assume that the angle between the camera 101 and the reflecting surface is an angle determined in advance. In this case, parameters such as the Fresnel reflection coefficient and a position relative to the camera, other than the micro facets coefficient m, are automatically determined based on the positional relationship between the camera 101 and the reflecting surface for each point on the reflecting surface. Hence, only the micro facets coefficient m is unknown in equation (2) for determining the intensity of specular reflection light at each point on the reflecting surface.

Only the micro facets coefficient m has an unknown value for each point of interest on the reflecting surface of the measurement target object 107. Thus, while changing the value of the micro facets coefficient m for each point of interest, equation (2) is solved to detect a value most properly expressing the specular reflection light component of an actual measurement value (solid line shown in FIG. 2B). The detected value is set as the micro facets coefficient m of the point of interest.

Figure 26A:
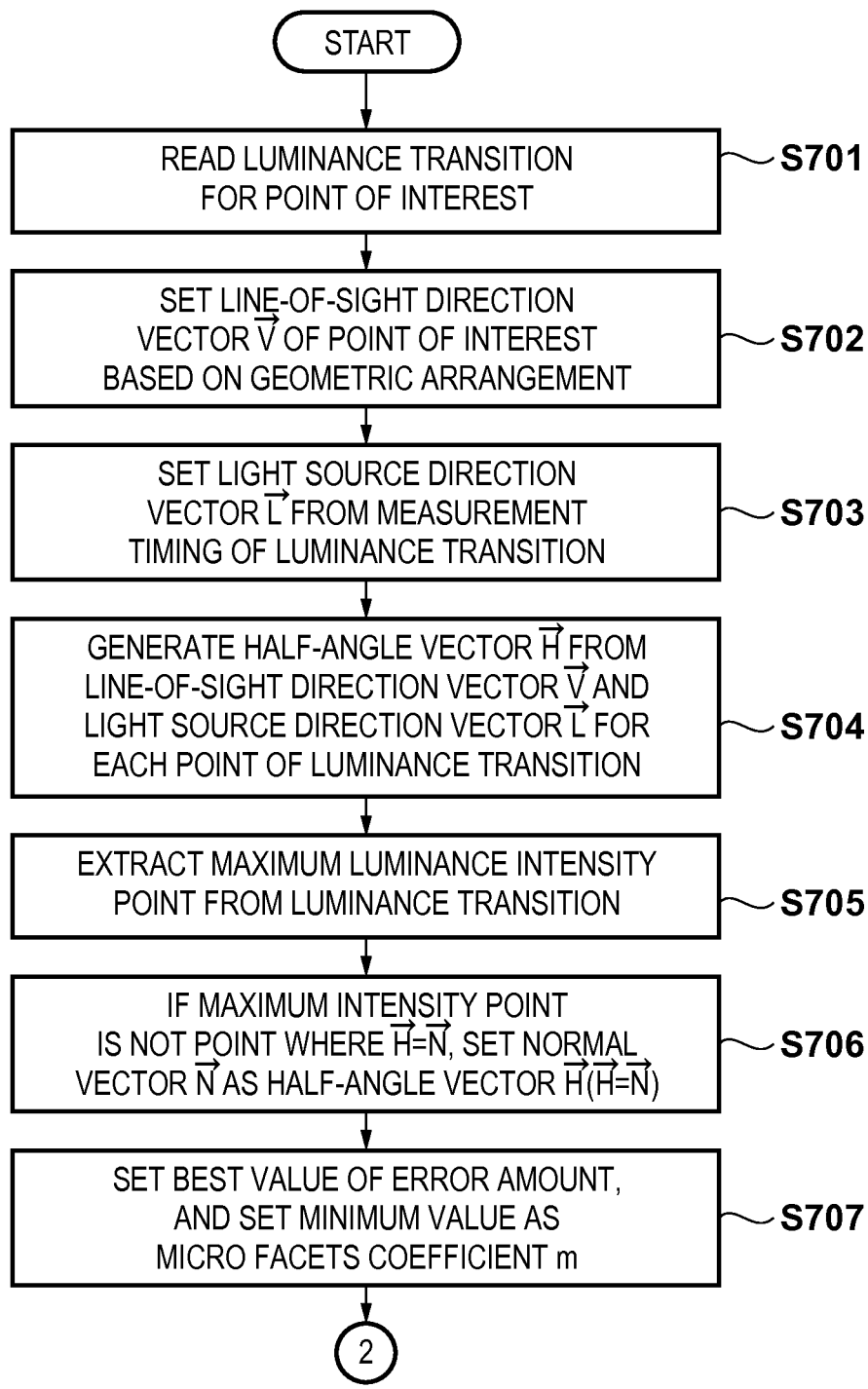
FIGS. 26A and 26B are flowcharts for explaining procedures to calculate a micro facets coefficient m.
Figure 26B:
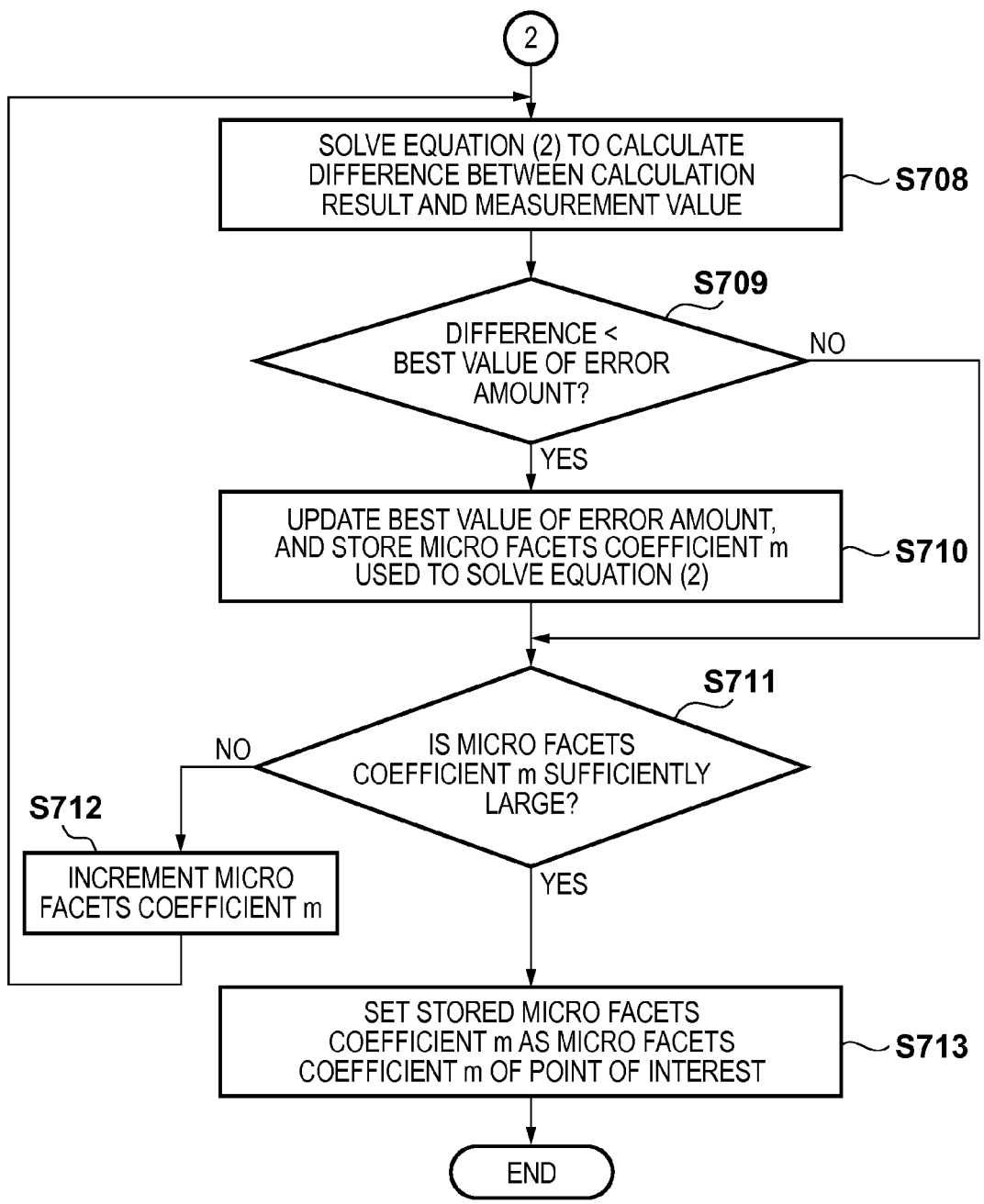

The procedures of calculation (S303) of the micro facets coefficient m will be explained with reference to the flowcharts of FIGS. 26A and 26B.

The luminance transition (solid line shown in FIG. 2B) is read for the point of interest (S701). The line-of-sight direction vector $\vec{V}$ of the point of interest is set based on the geometric arrangement (S702). The light source direction vector $\vec{L}$ is set from the measurement timing (abscissa shown in FIG. 2B) of the luminance transition (S703). For each point of the luminance transition, the half-angle vector $\vec{H}$ is generated from the line-of-sight direction vector $\vec{V}$ and light source direction vector $\vec{L}$ (S704). The maximum intensity point (specular reflection position) of the luminance is extracted from the luminance transition (S705). If the maximum intensity point is not a point where $\vec{H}=\vec{N}$, the half-angle vector $\vec{H}$ is set as the normal vector $\vec{N}$ ($\vec{H}=\vec{N}$) (S706).

The best value (initial value is, for example, INT_MAX) of the error amount for estimation is set, and the micro facets coefficient m is set to a minimum value (for example, 0.0001) (S707). Then, equation (2) is solved to calculate the difference between the calculation result and the measurement value (solid line shown in FIG. 2B) (S708). It is determined whether the difference is smaller than the best value of the error amount (S709). If the difference is smaller than the best value of the error amount, the best value of the error amount is updated by this difference, and the micro facets coefficient m used to solve equation (2) is stored (S710).

The micro facets coefficient m is incremented until it is determined in step S711 that the micro facets coefficient m used to solve equation (2) reaches a sufficiently large value (S712). Then, steps S708 to S710 are repeated. In this repetition, if the difference becomes smaller than the best value of the error amount, the stored micro facets coefficient m is updated in step S710. If the micro facets coefficient m has reached a sufficiently large value, the stored micro facets coefficient m is set as the micro facets coefficient m of the point of interest (S713). A broken line shown in FIG. 2B indicates a specular reflection light distribution obtained from the measurement value (solid line) shown in FIG. 2B.

Figure 27:
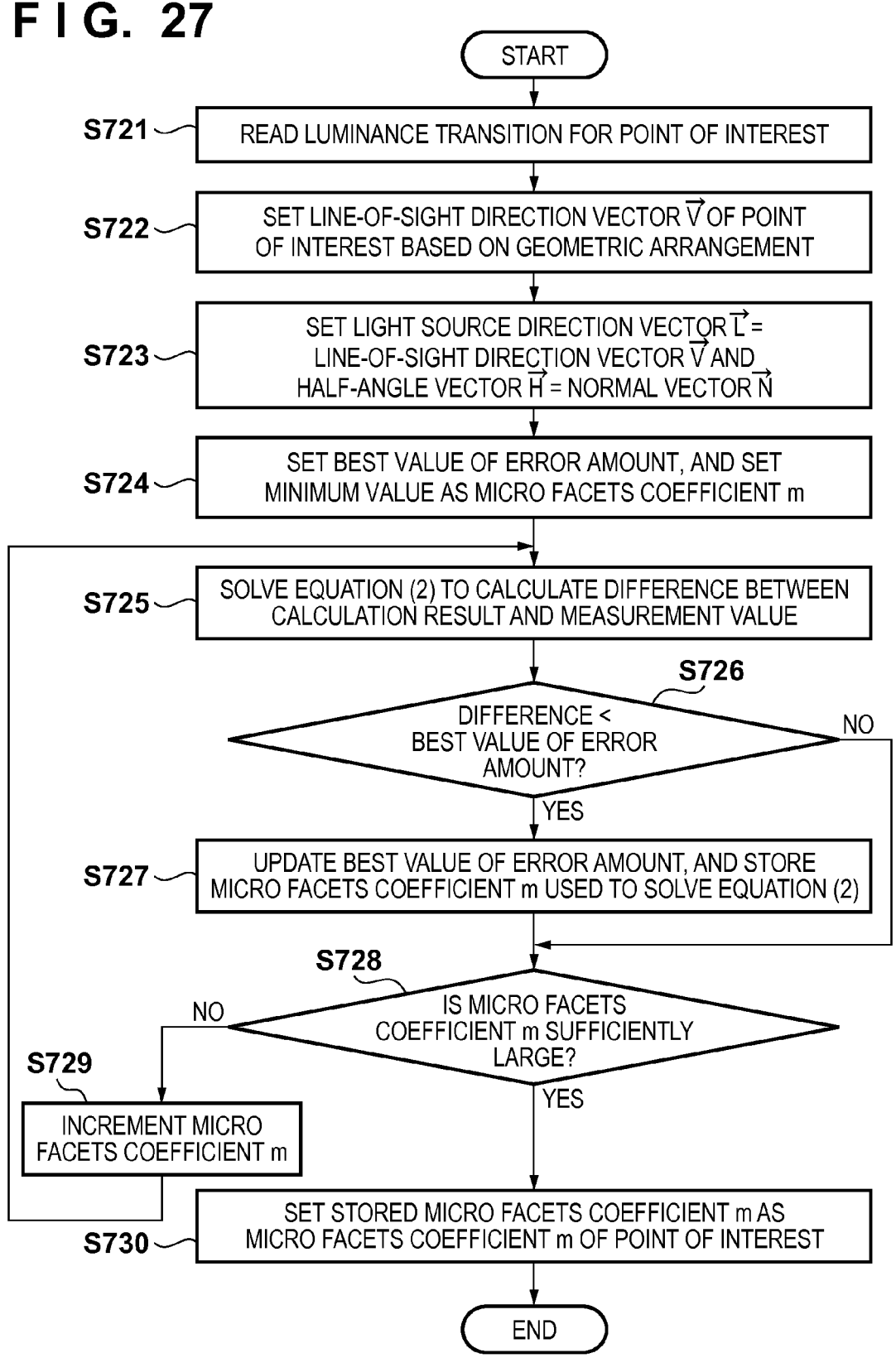
FIG. 27 is a flowchart for explaining procedures obtained by simplifying the procedures shown in FIGS. 26A and 26B.

Procedures obtained by simplifying the procedures shown in FIGS. 26A and 26B will be explained with reference to the flowchart of FIG. 27.

The luminance transition (solid line shown in FIG. 2B) is read for the point of interest (S721). The line-of-sight direction vector $\vec{V}$ of the point of interest is set based on the geometric arrangement (S722). The light source direction vector $\vec{L}$ is set as the line-of-sight direction vector $\vec{V}$ ($\vec{L}=\vec{V}$), and the half-angle vector $\vec{H}$ is set as the normal vector $\vec{N}$ ($\vec{H}=\vec{N}$) (S723).

The best value (initial value is, for example, INT_MAX) of the error amount for estimation is set, and the micro facets coefficient m is set to a minimum value (for example, 0.0001) (S724). Then, equation (2) is solved to calculate the difference between the calculation result and the measurement value (solid line shown in FIG. 2B) (S725). It is determined whether the difference is smaller than the best value of the error amount (S726). If the difference is smaller than the best value of the error amount, the best value of the error amount is updated by the difference, and the micro facets coefficient m used to solve equation (2) is stored (S727).

The micro facets coefficient m is incremented until it is determined in step S728 that the micro facets coefficient m used to solve equation (2) reaches a sufficiently large value (S729). Then, steps S725 to S727 are repeated. In this repetition, if the difference becomes smaller than the best value of the error amount, the stored micro facets coefficient m is updated in step S728. If the micro facets coefficient m has reached a sufficiently large value, the stored micro facets coefficient m is set as the micro facets coefficient m of the point of interest (S730).

In this manner, minimum scanning is performed by controlling the scanning length of the line light source 104 in accordance with conditions such as the size (length), type (paper type or material), and rough gloss information (visual perception of the material) of the measurement target object 107 (or reflecting surface). This can minimize the time to acquire the BRDF distribution of the reflecting surface of the measurement target object 107.

Second Embodiment

Measurement of optical characteristics according to the second embodiment of the present invention will be described below. In the second embodiment, the same reference numerals as those in the first embodiment denote the same parts, and a detailed description thereof will not be repeated.

[Outline of Apparatus]

FIG. 9 shows an outline of a measurement apparatus according to the second embodiment. The measurement apparatus according to the second embodiment uses an emission display 114 such as a liquid crystal panel for formation of a light source of line shape, instead of the line light source 104 of the measurement apparatus according to the first embodiment shown in FIG. 1.

In the second embodiment, a plurality of line patterns are displayed on the display 114, and the display of the line patterns is moved to illuminate the reflecting surface of a measurement target object 107. A camera 101 captures the light reflected by the reflecting surface as an image, measuring the BRDF distribution of the reflecting surface.

The second embodiment is therefore different from the first embodiment in control of the line patterns displayed on the display 114 by a light source control unit 102 because the light source moving unit 103 is unnecessary. The second embodiment is also different from the first embodiment in processing of a BRDF estimation unit 105.

Decision of Number of Line Patterns

Figure 10B:
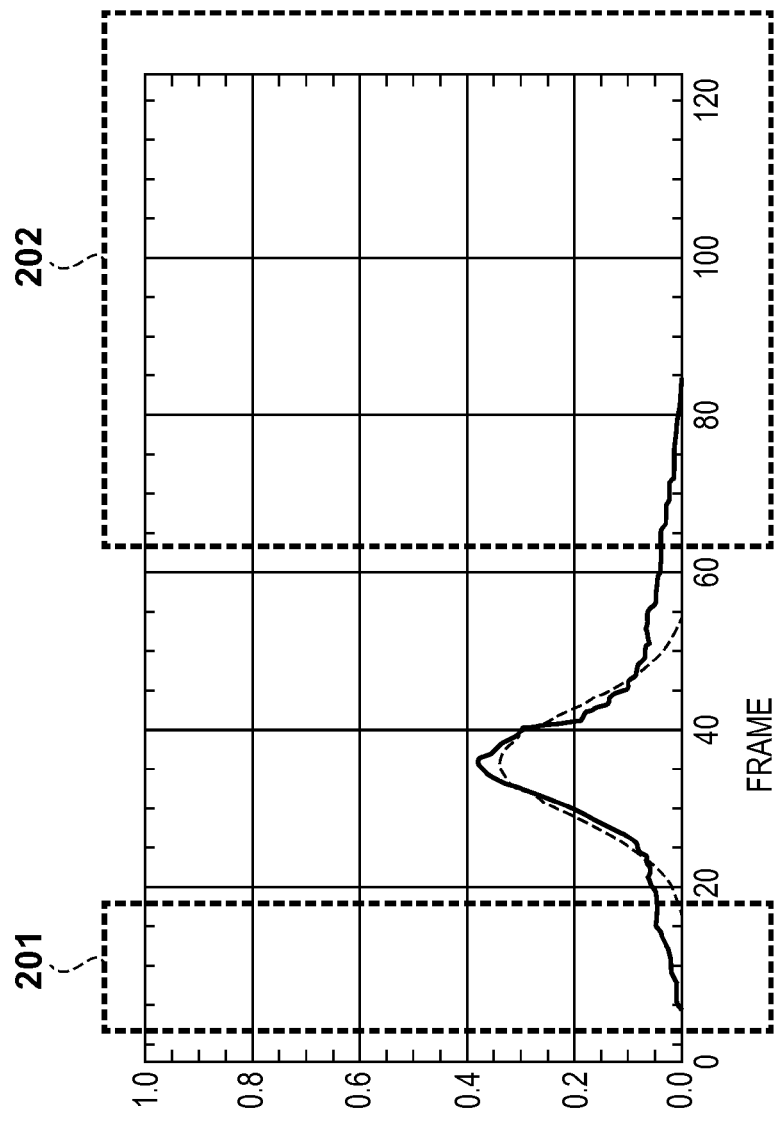
FIGS. 10A and 10B are graphs showing an example of the luminance transition obtained from points on the reflecting surface by scanning the line light source.
Figure 10A:
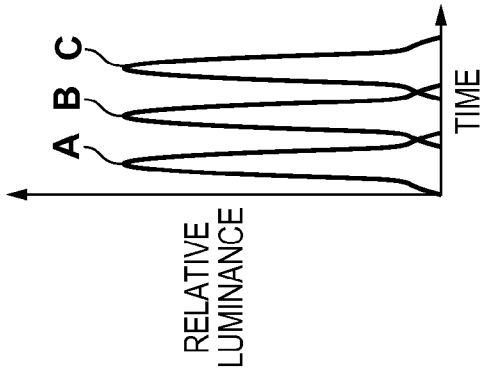

FIGS. 10A and 10B show an example of the luminance transition (captured by the camera 101) obtained from points on the reflecting surface by scanning a line light source 104.

FIG. 10A is a graph showing an example of luminance transitions at three points A, B, and C of interest on the reflecting surface of the measurement target object 107. FIG. 10B shows, for example, the luminance transition at the point A of interest. The BRDF (specular reflection light component) of the point A of interest is measured from luminances before and after a luminance peak corresponding to the specular reflection angle. In contrast, a diffuse light component is measured from the periphery at which the angle differs from the specular reflection angle and the luminance is not excessively low. In other words, broken-line regions 201 and 202 in FIG. 10B are unnecessary for measurement of the BRDF of the point A of interest. A region necessary to measure the BRDF of the point A of interest is only a region around the peak of the luminance transition, which is not surrounded by a broken line.

Further, the fact that the diffuse light component is small in the regions 201 and 202 indicates that the influence of a diffuse light component from the region 201 or 202 on a captured image in the region of interest on the reflecting surface can be ignored even when the line light source 104 exists at a scanning position corresponding to the region 201 or 202. That is, even if illumination light exists in a region satisfactorily outside by the spread amount B of the specular reflection light component, it does not influence measurement of the BRDF (specular reflection light component). Since the diffuse light component is isotropic, a plurality of line patterns are possible as long as they are positioned at a predetermined interval.

Considering this, the control unit 100 controls the light source control unit 102 to simultaneously display a plurality of line patterns and move them so as not to influence measurement of the BRDF, thereby shortening the BRDF measurement time. That is, the number and interval of line patterns are controlled in accordance with conditions such as the size, type (paper type or material), and rough gloss information (visual perception of the material) of the measurement target object 107 (or reflecting surface).

FIG. 11 shows a display example of the display 114. For example, the spread amount B of the specular reflection light component is set from gloss information, an interval P between line patterns 115 is set to be equal to or larger than triple the spread amount B, and the number of line patterns 115 is decided. By moving the display of the plurality of line patterns 115 having the cycle P≥3B in a direction indicated by an arrow shown in FIG. 11, the BRDFs of all points on the reflecting surface are measured to measure the BRDF distribution in a short time.

In this fashion, the interval P and number of the line patterns 115 are controlled in accordance with the type (paper type or material) and rough gloss information (visual perception of the material) of the measurement target object 107 (or reflecting surface). As a result, capturing of the measurement target object 107 ends in a minimum time necessary to measure the BRDF of the measurement target object 107.

Decision of Width of Line Pattern

By using the display 114, the width and brightness of a line pattern to be scanned can be changed in consideration of the illuminance of the reflecting surface and the aperture angle. For example, if the width of the line pattern is set to be 1/10 of the spread amount B, the width becomes large when the spread amount B is large. Thus, the illuminance of the reflecting surface can be increased, the exposure time of the capturing unit 101 can be shortened, and the measurement time can be shortened.

The width of the line pattern may be changed in accordance with the location so that the aperture angle with respect to a given line of the measurement target object 107 becomes constant. The aperture angle is a width when the light source is viewed from a given line of the measurement target object 107. A large aperture angle indicates a large amplitude (aperture angle) ±Δθ of the incident angle θ. That is, if the aperture angle Δθ is large, light beams traveling from various directions enter the measurement target object 107, so the resolution of the BRDF with respect to the variable angle decreases (which is equivalent to so-called "blur of the BRDF").

When scanning thick line patterns, if the width is constant, the aperture angle when viewed from a given line changes depending on the scanning position. As a result, the resolution of the BRDF to be measured with respect to the variable angle changes depending on the incident angle θ. By changing the width in accordance with the scanning position, the resolution can be kept constant.

An example of controlling the widths of line patterns in accordance with the scanning position will be explained.

Figure 28:
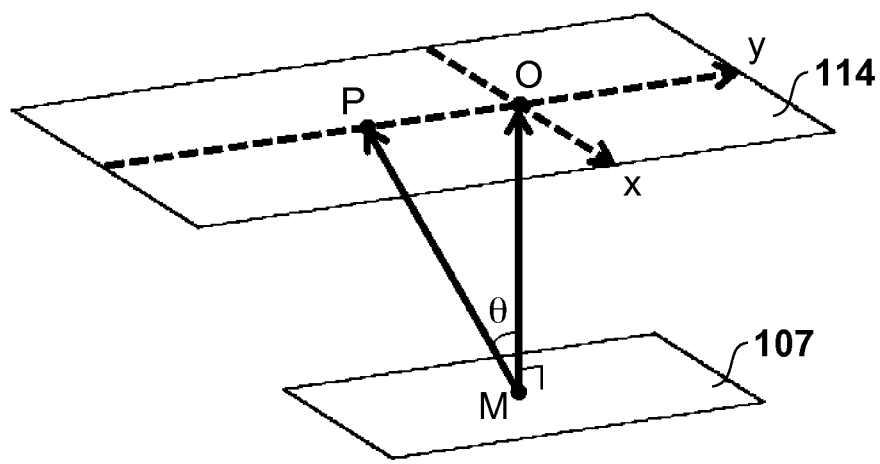
FIG. 28 is a view illustrating the geometric condition of the display and reflecting surface.

FIG. 28 shows the geometric condition of the display and reflecting surface. As shown in FIG. 28, let M be an arbitrary point on the measurement target object 107, and O be a point at which a normal extending from the point M crosses the surface of the display 114. Also, let a direction parallel to the line pattern be the x-axis, and the line pattern scanning direction be the y-axis. Then, a width Δy of the line pattern at a scanning position P of the line pattern on the y-axis is given by:

$$\Delta y = ||OM| \cdot \{\tan(\theta+\Delta\theta) - \tan(\theta-\Delta\theta)\}| \quad (6)$$

where
$\theta = \tan^{-1}(|OP|/|OM|)$,
|OM| is the distance between the display 114 and the measurement target object 107,
|OP| is the distance between the point O and the scanning position P, and
Δθ is the aperture angle (constant set in advance, for example, calculated from the spread amount B).

Figure 29:
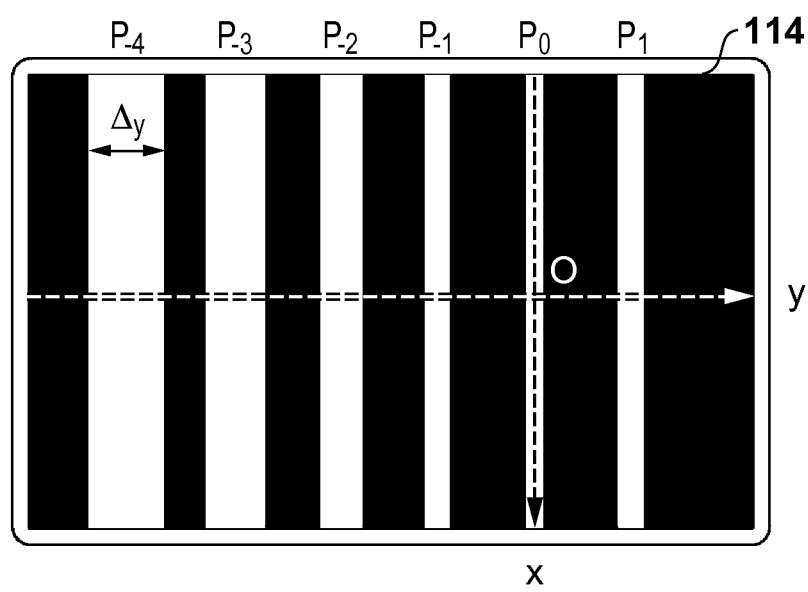
FIG. 29 is a view illustrating the emission pattern of the display.

When Δy is decided in this manner, the BRDF can be measured while keeping the aperture angle Δθ constant regardless of the scanning position P of the line pattern. The emission pattern of the display will be explained with reference to FIG. 29. By the above-described control, the width Δy of the line pattern changes depending on the scanning position P on the display 114, as shown in FIG. 29.

Other Patterns

By using the display 114, an emission pattern other than the line pattern can be scanned to measure the BRDF. For example, by two-dimensionally scanning a point or circular emission pattern, a BRDF when a light source vector L moves two-dimensionally can be measured.

An example of performing two-dimensional scanning using an elliptic pattern will be explained.

FIG. 30 shows the geometric condition of the display and reflecting surface. As shown in FIG. 30, the center of the elliptic pattern is defined as a point P. The position of the point P is scanned on the display 114 to move the light source vector L ($=\overrightarrow{PM}$) two-dimensionally in the direction of an angle θ and the direction of an angle φ. At this time, an x-coordinate Px and y-coordinate Py of the point P are given by:

$$Px(\theta,\phi)) = |OM| \cdot \tan\theta \cdot \cos\phi \quad (7)$$

$$Py(\theta,\phi) = |OM| \cdot \tan\theta \cdot \sin\phi \quad (8)$$

Even in this case, the size of the elliptic pattern can be changed in accordance with the scanning position P so that the aperture angle Δθ in the θ direction and the aperture angle Δφ in the φ direction become constant regardless of the scanning position P. For example, a diameter $\Delta D_\theta$ of the elliptic pattern in the θ direction ($\overrightarrow{PO}$ direction) and a diameter $\Delta D_\phi$ in the φ direction (direction perpendicular to the $\overrightarrow{PO}$ direction) can be calculated by:

$$\Delta D_\theta = \sqrt{[\{(Px(\theta+\Delta\theta,\phi)-Px(\theta-\Delta\theta,\phi))^2+\{Py(\theta+\Delta\theta,\phi)-Py(\theta-\Delta\theta,\phi)\}^2\}]} \quad (9)$$

$$\Delta D_\phi = \sqrt{[\{(Px(\theta,\phi+\Delta\phi)-Px(\theta,\phi-\Delta\phi))^2+\{Py(\theta,\phi+\Delta\phi)-Py(\theta,\phi-\Delta\phi)\}^2\})} \quad (10)$$

The emission pattern of the display will be explained with reference to FIG. 31. By the above-described control, the size of the elliptic pattern can be changed depending on the scanning position P on the display 114. Scanning of the point P can be performed by various methods such that, for example, the scanning is performed to change the angles θ and φ at equal pitches or is performed at equal pitches along the x- and y-axes, respectively. The BRDF can also be measured in the entire region of the measurement target object 107 by repeating scanning several times in accordance with the position of the point M on the measurement target object 107.

Further, by using the display 114, the emission luminance of the emission pattern can be easily changed in accordance with the scanning position P. For example, an illuminance meter (or its sensor) is placed at the point M on the measurement target object 107. A luminance control signal of the display 114 that corresponds to each scanning position is generated so that the illuminance at the point M becomes constant. The correspondence between each scanning position and the luminance control signal is recorded in a lookup table. In scanning, the lookup table is looked up to decide a luminance control signal of the display 114 that corresponds to the scanning position. This can make the illuminance at the point M constant. Therefore, the luminance range (dynamic range) in which the capturing unit 101 receives light becomes narrow, and a lower-cost image sensor can be used. Also, the exposure time of the image sensor can be shortened to speed up measurement.

[Measurement Apparatus Using Tablet Device]

FIG. 9 shows the measurement apparatus including the display 114 on which the line patterns 115 are displayed and scanned, and the camera 101 which captures light reflected by the reflecting surface. However, a tablet device serving as a computer device including a camera on the same surface as the display screen is usable as the measurement apparatus. The use of the tablet device will be exemplified below. For descriptive convenience, the number of line patterns 115 is one.

Figure 12:
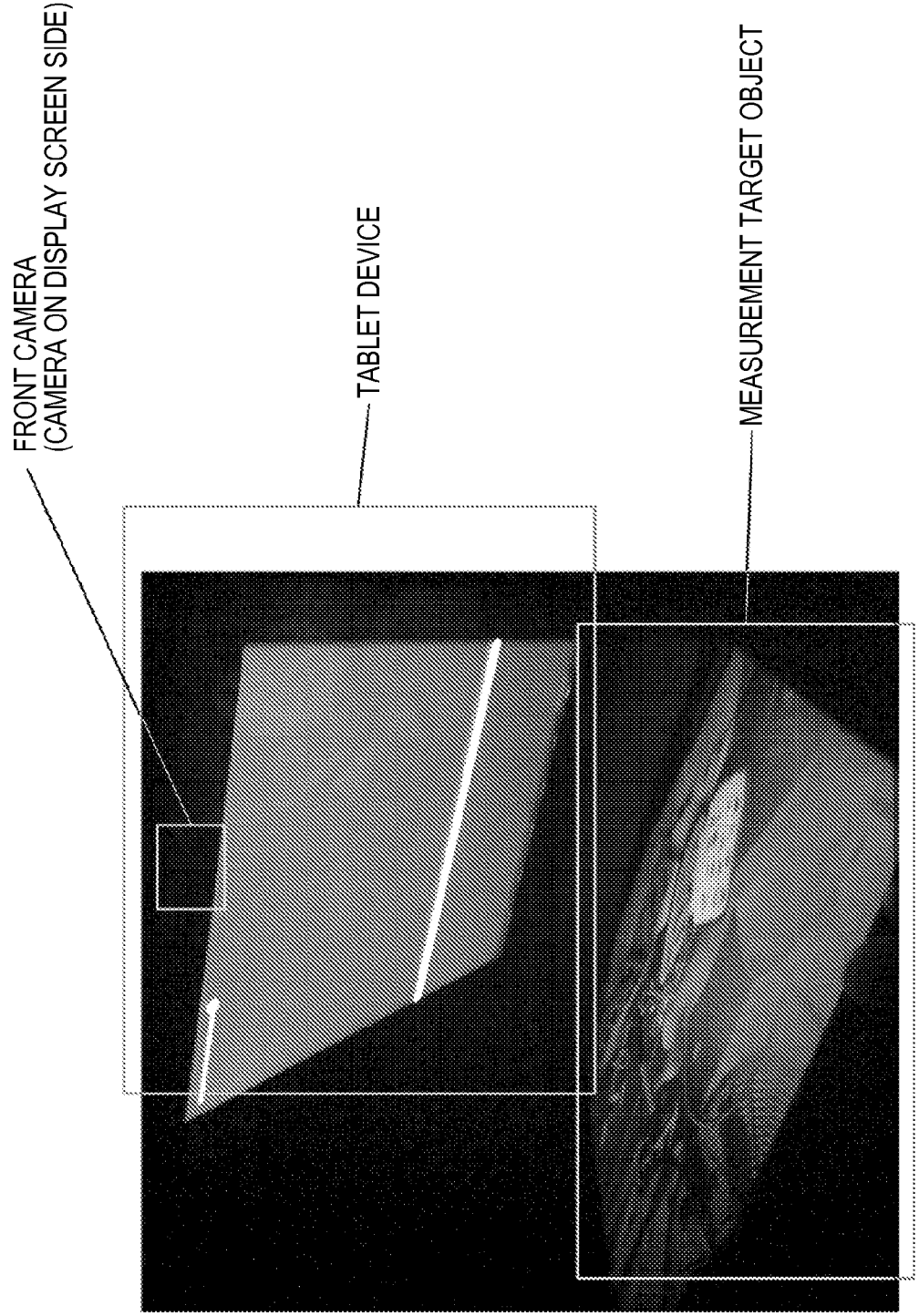
FIG. 12 is a view showing a measurement apparatus using a tablet device.

FIG. 12 shows a measurement apparatus using a tablet device. More specifically, the tablet device is arranged to face the measurement target object 107. The line pattern 115 is displayed and scanned on the screen, and the camera on the display screen side (to be referred to as a "front camera" hereinafter) captures light reflected by the measurement target object 107 (or reflecting surface) to measure the BRDF distribution.

BRDF measurement procedures using the tablet device will be explained with reference to FIGS. 13A to 13F. First, the tablet device is arranged to face the measurement target object 107 in a dark place where there is no influence of another illumination.

Figure 13A:
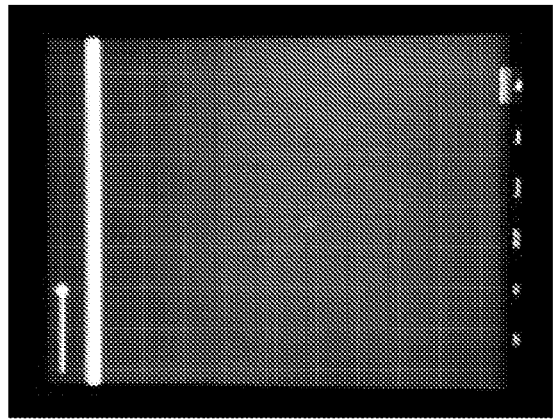
FIGS. 13A to 13F are views for explaining BRDF measurement procedures using the tablet device.
Figure 13B:
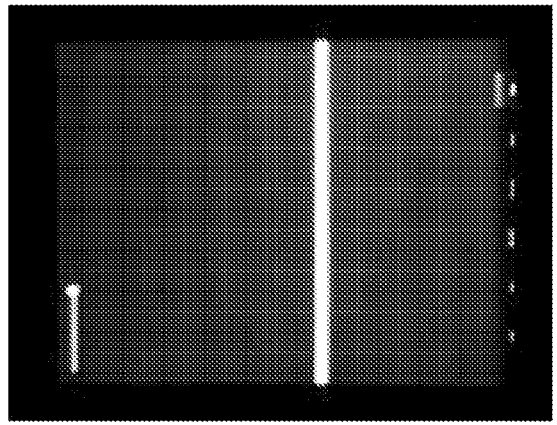
Figure 13C:
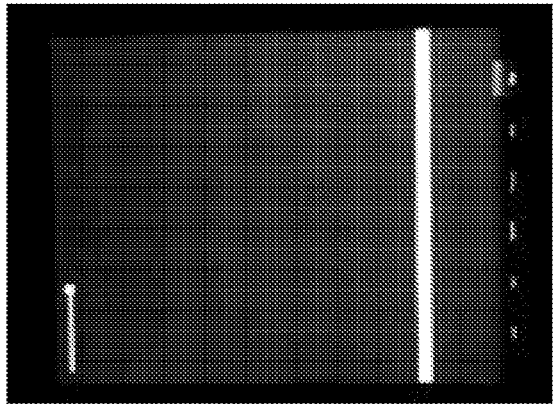
Figure 13D:
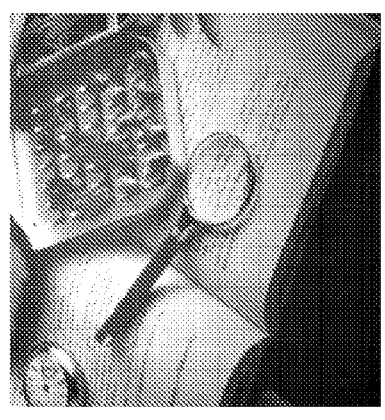
Figure 13E:
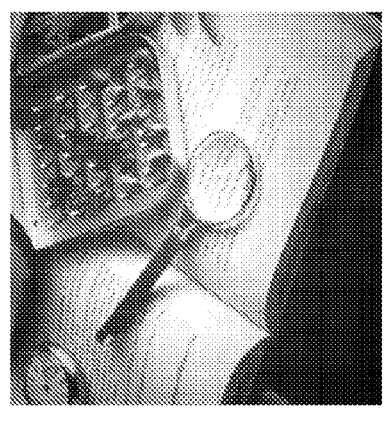
Figure 13F:
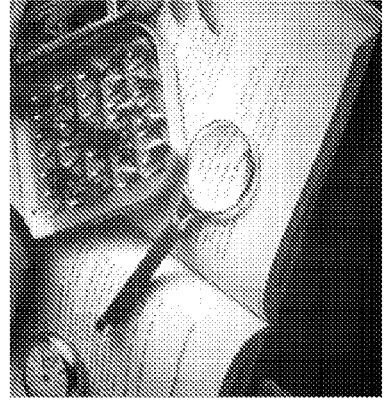

Then, the line pattern 115 on a black background is displayed on the screen of the tablet device. The display is presented so that the line pattern 115 is moved (scanned) along a straight line connecting the center of the screen and the front camera (FIGS. 13A to 13C). During the scanning of the line pattern 115, the measurement target object 107 illuminated with light of the line pattern 115 is sequentially captured. FIGS. 13D to 13F show examples of sequentially captured images. By these procedures, the luminance distribution of the measurement target object 107 (or its reflecting surface) illuminated from various angles is captured by using the line pattern 115 moving on the screen.

Figure 14:
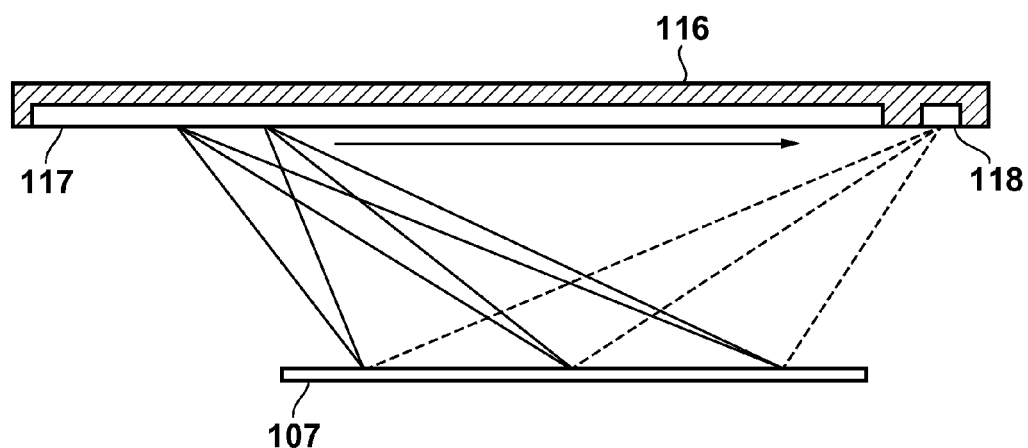
FIG. 14 is a view for explaining the positional relationship between the tablet device and the reflecting surface of a measurement target object in measurement.

The positional relationship between a tablet device 116 and the reflecting surface of the measurement target object 107 in measurement will be explained with reference to FIG. 14. When the line pattern 115 moves on a screen 117 of the tablet device 116, the incident angle of light traveling from the line pattern 115 with respect to each point on the reflecting surface changes. To the contrary, the positional relationship between each point and a front camera 118 does not change, and the position of each point in the captured image does not change. That is, a point on the reflecting surface is always captured at the same angle (direction) from the front camera 118. Reflected light (or diffuse light) captured for a given point is always captured at an angle (radiation angle) defined by the point.

Figure 15:
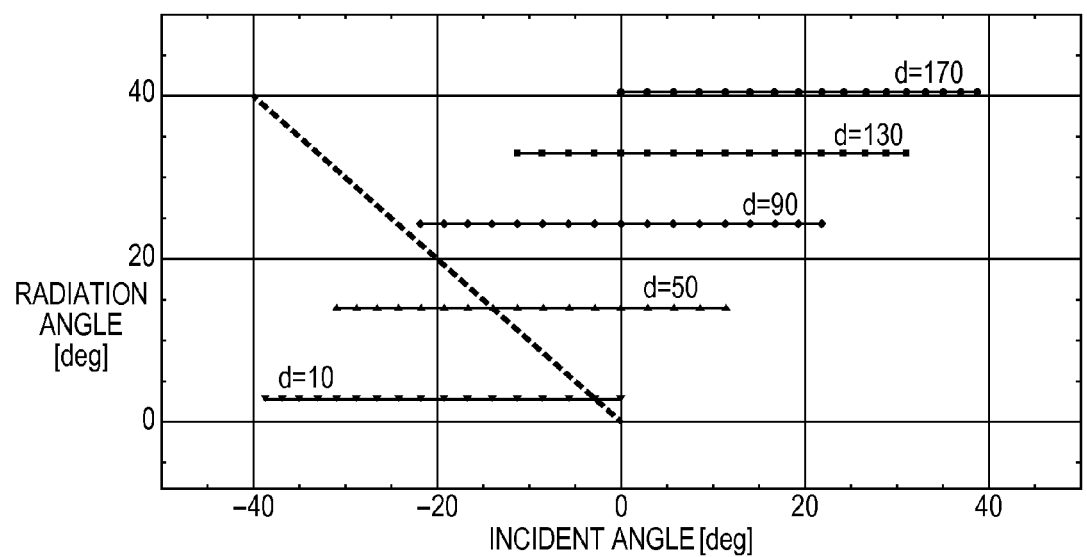
FIG. 15 is a graph showing relationships between the light incident angle and the radiation angle at respective points on the reflecting surface that have different distances from a front camera.

FIG. 15 shows relationships between the light incident angle (abscissa) and the radiation angle (ordinate) at respective points on the reflecting surface that have different distances d from the front camera 118. Note that the angle is 0° in a direction perpendicular to the reflecting surface. A thick broken line shown in FIG. 15 indicates a specular reflection condition (incident angle=radiation angle). The distance d (unit: mm) shown in FIG. 15 is merely an example.

If capturing is performed at the same time as scanning of the line pattern 115, the variable angle luminous intensity distribution of reflected light on the reflecting surface (each point) of the measurement target object 107 is measured sequentially. The variable angle luminous intensity distribution of the specular reflection component is measured at a point where the angle matches the specular reflection condition indicated by the thick broken line in FIG. 15. FIGS. 16A to 16C show a luminance change (that is, variable angle luminous intensity distribution) of pixels corresponding to several points on the reflecting surface of the measurement target object 107. As shown in FIG. 16A, variable angle luminous intensity distributions (luminance transition) (for different incident angles) are measured at points on the reflecting surface. FIGS. 16B and 16C schematically show the correspondence between the luminance transition at each point and the BRDF section.

Figure 17A:
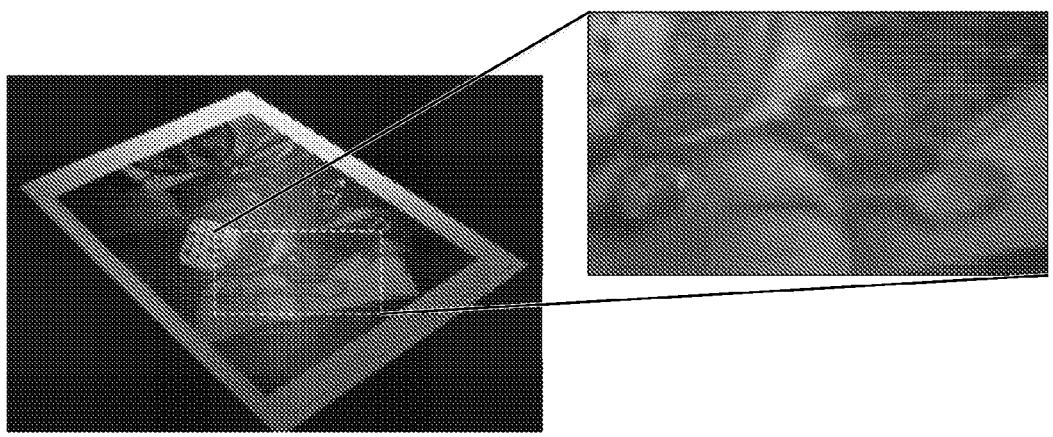
FIGS. 17A to 17C are views showing the measurement target object and its measurement result.
Figure 17B:
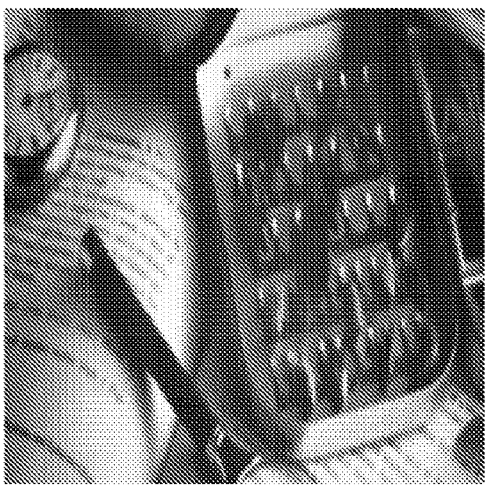
Figure 17C:
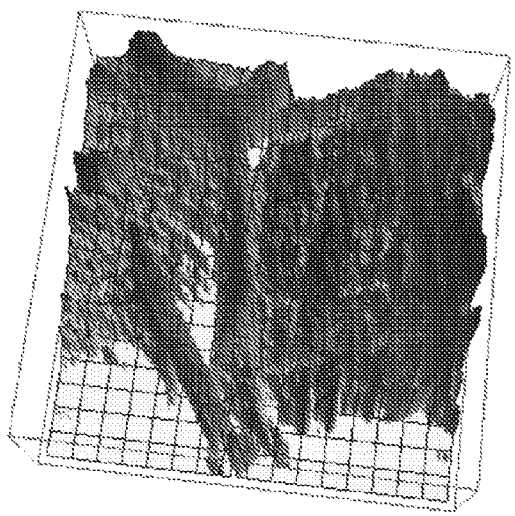

FIGS. 17A to 17C show the measurement target object 107 and its measurement result. The measurement target object 107 shown in FIG. 17A is a material printed by an electrophotographic method under a high-gloss condition. Part (enlarged part) of the printed material is measured, obtaining a diffuse color distribution shown in FIG. 17B and a BRDF distribution shown in FIG. 17C. A gloss distribution reflecting the amount of applied toner is measured.

FIGS. 18A to 18C show an example of CG rendering using the measured BRDF distribution. By performing CG rendering, the appearance of the reflecting surface of the measurement target object 107 can be reproduced on the screen (FIG. 18A). FIGS. 18B and 18C show CG rendering when the reflecting surface of the measured measurement target object 107 is observed from a different observation direction.

BRDF Distribution Capturing Processing

Figure 19A:
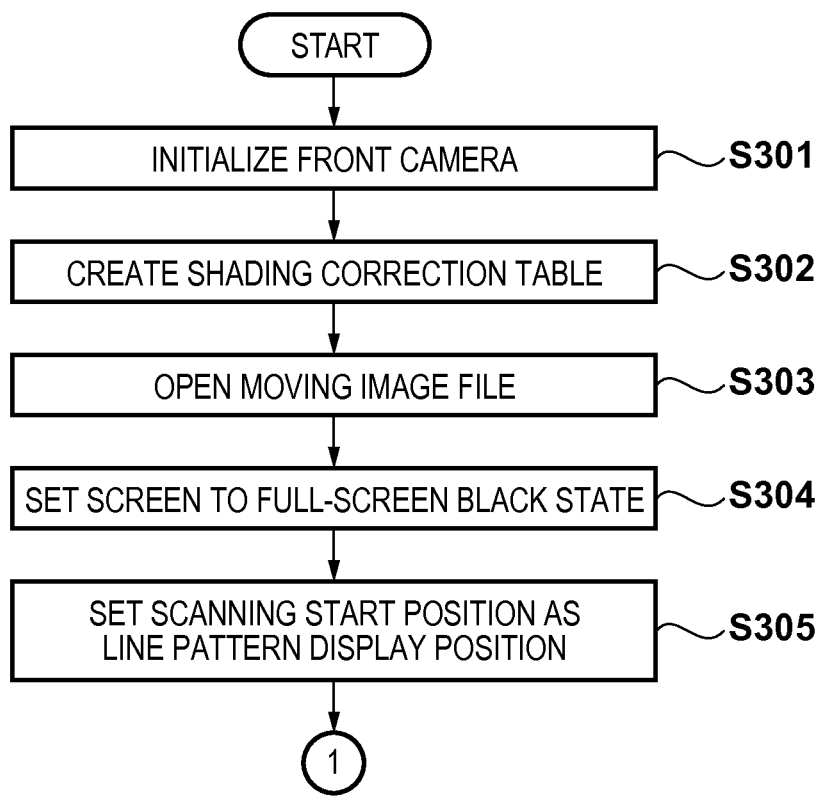
FIGS. 19A to 21 are flowcharts for explaining an example of BRDF distribution capturing processing.
Figure 19B:
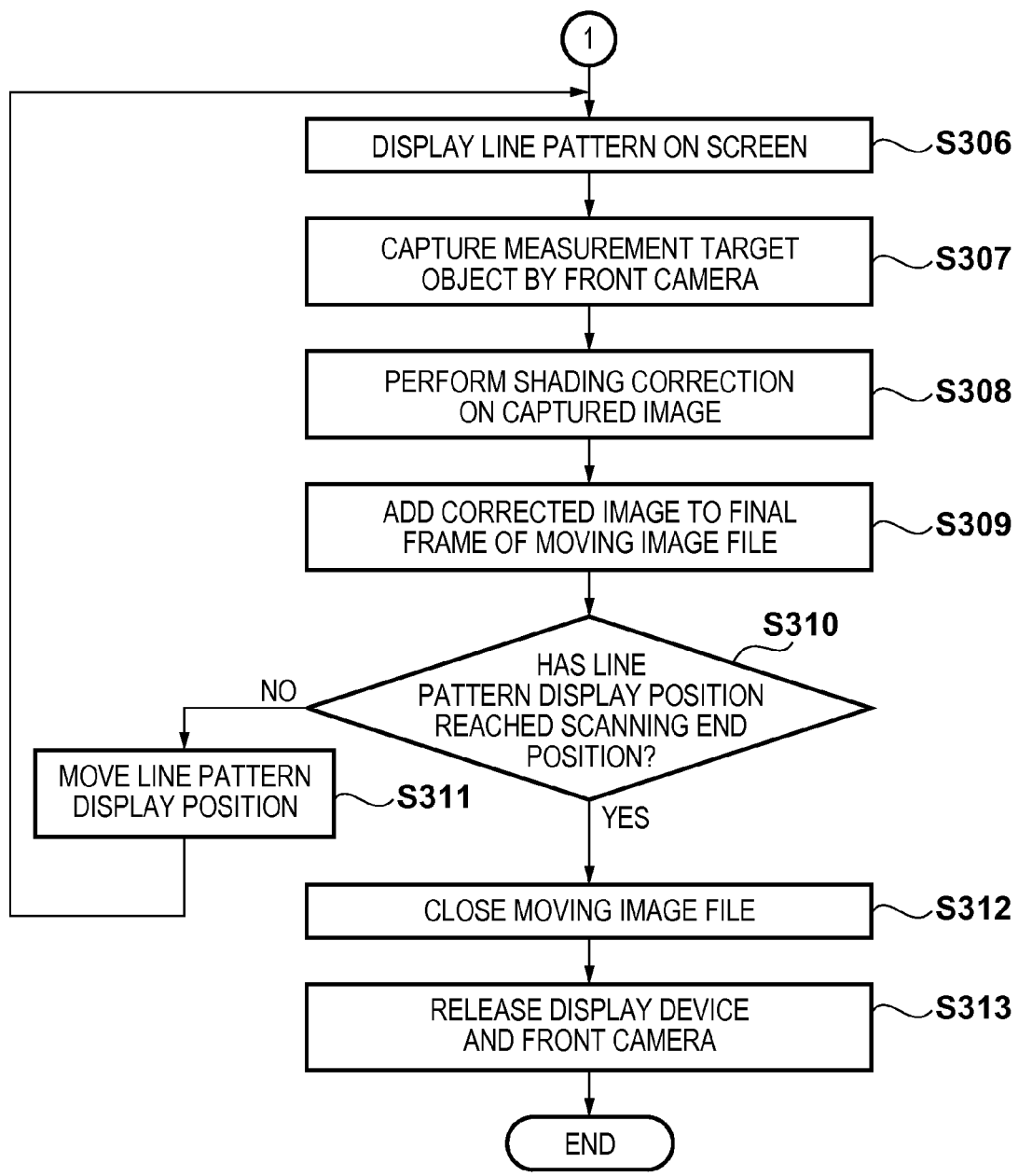

An example of BRDF distribution capturing processing will be explained with reference to the flowcharts of FIGS. 19A and 19B. The following processing and function are implemented by executing a BRDF distribution capturing program by the microprocessor (CPU) of the tablet device 116 after the user designates capturing of the BRDF distribution.

The CPU initializes the front camera 118 to lock the focus and stop of the front camera 118 (S301), and creates a luminance correction (shading correction) table from the focus position (S302). Then, the CPU opens a moving image file for saving a captured image (S303), sets the screen 117 in a full-screen black state (S304), and sets a scanning start position as the display position of the line pattern 115 (S305). Note that the flash memory of the tablet device 116 or the like is assigned as a moving image file save destination.

The CPU displays the line pattern 115 on the screen 117 (S306), and controls the front camera 118 to capture the measurement target object 107 (S307). FIG. 23A shows an example of the measurement target object 107. The CPU performs shading correction on the captured image (S308), and adds the corrected image to the final frame of the moving image file (S309).

The CPU determines whether the display position of the line pattern 115 has reached a scanning end position (S310). If the display position has not reached the scanning end position, the CPU moves the display position of the line pattern 115 (S311), and returns the process to step S306. If the display position of the line pattern 115 has reached the scanning end position, the CPU closes the moving image file (S312), releases the display device and the front camera 118 (S313), and ends the capturing processing.

BRDF Distribution Calculation Processing

Figure 20:
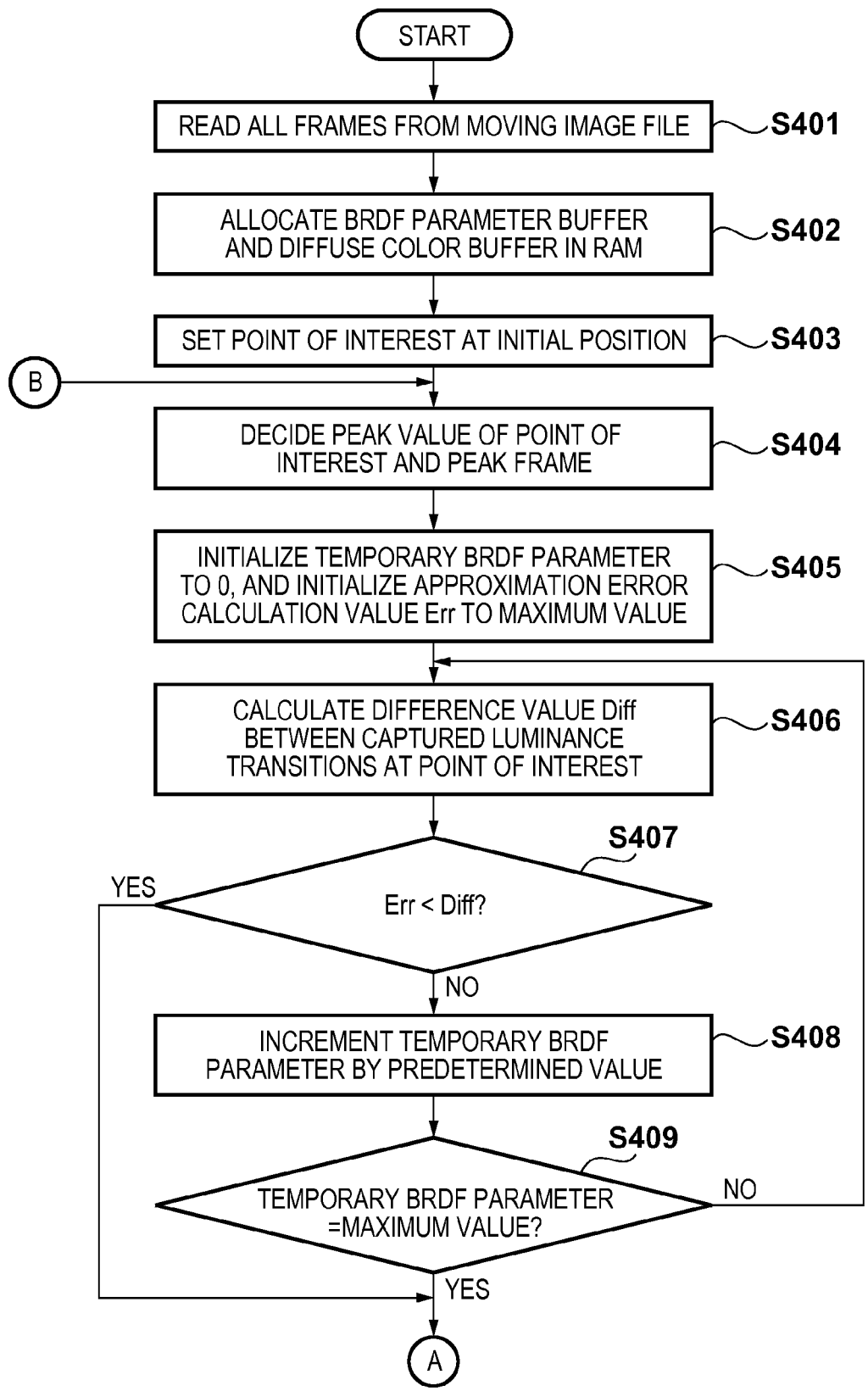
Figure 21:
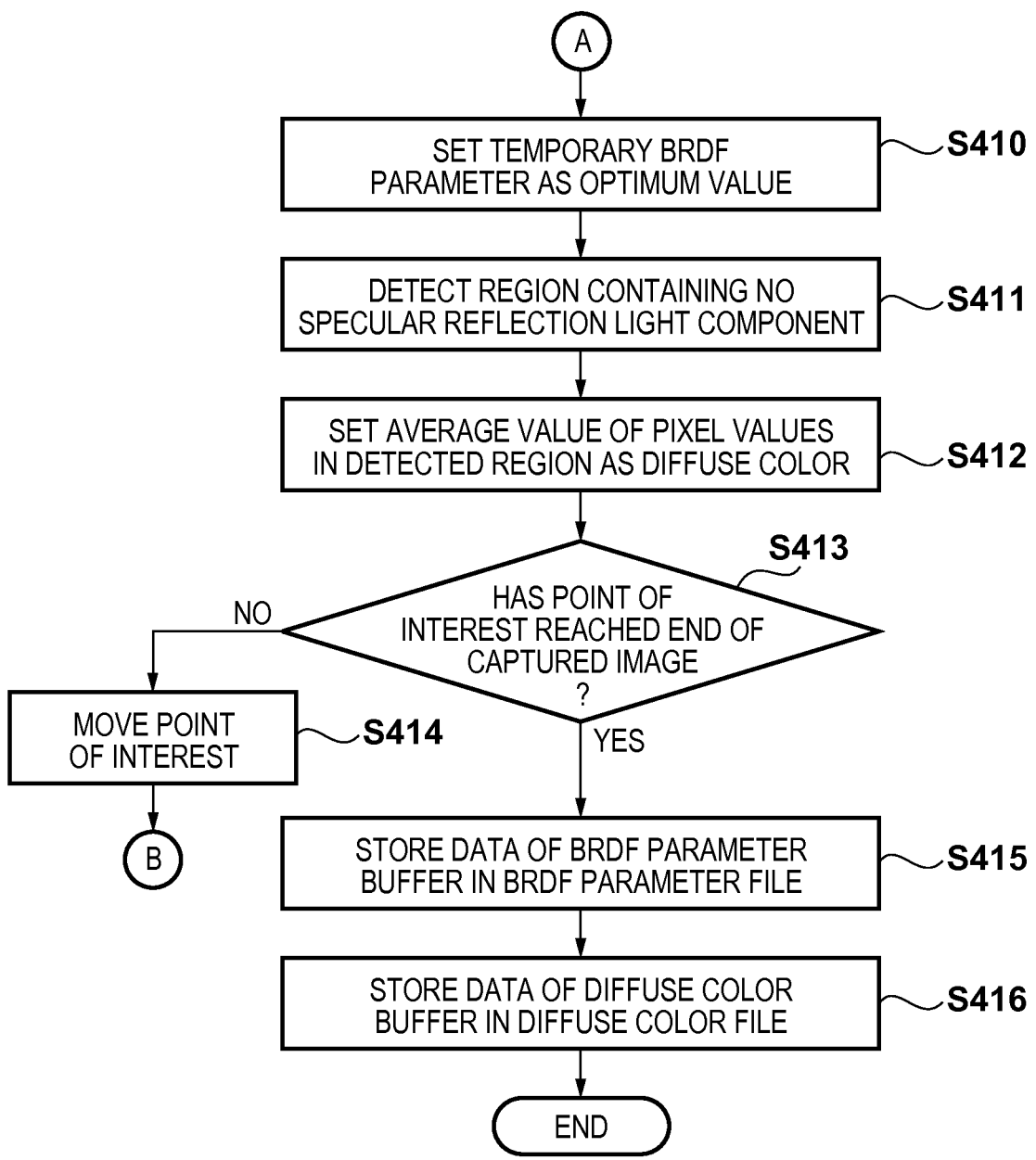

An example of BRDF distribution calculation processing will be described with reference to the flowcharts of FIGS. 20 and 21. The following processing is implemented by executing a BRDF distribution calculation program by the CPU of the tablet device 116 after the end of capturing the BRDF distribution.

The CPU reads all frames from a moving image file (S401), and allocates, in the RAM of the tablet device 116, a BRDF parameter buffer and diffuse color buffer each of the same size as that of a captured image (S402). Then, the CPU sets the point of interest at an initial position (for example, the upper left pixel of the image) (S403).

The CPU refers to the pixel value of the point of interest from the first frame to the final frame, and decides the peak value of the pixel value and a frame representing the peak value (to be referred to as a "peak frame" hereinafter) (S404). The CPU initializes the temporary BRDF parameter to 0, and an approximation error calculation value Err to a maximum value (S405).

The CPU calculates a difference value Diff between captured luminance transitions at the point of interest when the temporary BRDF parameter is substituted into the BRDF equation (S406). The CPU compares the difference value Diff with the approximation error calculation value Err (S407). If Diff≥Err, the CPU increments the temporary BRDF parameter by a predetermined value (S408). The CPU determines whether the temporary BRDF parameter has reached a predetermined maximum value (S409). If the temporary BRDF parameter has not reached the maximum value, the CPU returns the process to step S406.

If Err<Diff in the comparison of step S407, or if the temporary BRDF parameter has reached the maximum value, the CPU sets the temporary BRDF parameter as an optimum value, and stores this value in an area of the BRDF parameter buffer that corresponds to the point of interest (S410). FIG. 23C shows an example of the BRDF parameter (BRDF distribution).

Based on the peak value and peak frame, the CPU detects a region (for example, the region 201 or 202 shown in FIG. 10) containing no specular reflection light component (S411). The CPU stores, as a diffuse color, the average value of pixel values in this region in an area of the diffuse color buffer that corresponds to the point of interest (S412). FIG. 23B shows an example of the diffuse color distribution.

The CPU determines whether the point of interest has reached the end (for example, the lower right pixel of the image) of the captured image (S413). If the point of interest has not reached the end of the captured image, the CPU moves the point of interest in, for example, the raster order (S414), and returns the process to step S404.

If the point of interest has reached the end of the captured image, the CPU stores data of the BRDF parameter buffer in a BRDF parameter file (S415), stores data of the diffuse color buffer in a diffuse color file (S416), and ends the calculation processing. Note that the BRDF parameter file and diffuse color file are stored in, for example, the flash memory of the tablet device 116 or a storage device connected to a wireless network.

CG Rendering Preview Processing

An example of CG rendering preview processing will be explained with reference to the flowchart of FIG. 22. The following processing is implemented by executing a CG rendering preview program by the CPU of the tablet device 116 after the end of calculating the BRDF distribution.

The CPU reads the diffuse color file and BRDF parameter file (S501), creates a diffuse color texture and BRDF parameter texture (S502), and creates a vertex shader and fragment shader (S503).

The CPU initializes the relative coordinates of the illumination, display, and viewpoint (S504), initializes the display device and display context (S505), and executes rendering to display the preview of CG rendering on the screen 117 (S506). FIG. 23D shows an example of the preview screen.

The CPU determines a user event and a state change of tablet device 116 (S507). If a print instruction is input, the CPU copies the display context to an image buffer, outputs RGB data in the image buffer to a printer through, for example, a wireless network (S508), and returns the process to step S506. If an end instruction is input, the CPU closes the display context, releases the display device (S509), and ends the preview processing.

If another user event is input or the state of the tablet device 116 changes, the CPU updates, for example, the relative coordinates of the illumination, display, and viewpoint in accordance with the event or the state change (S510), and returns the process to step S506.

Print Processing

In printing (S508) in the preview processing, the CPU can output, to the printer, color component data (to be referred to as "CL data" hereinafter) for a transparent color material (or clear color material) based on the BRDF parameter texture, in addition to RGB data of the diffuse color texture stored in the image buffer. FIG. 23E shows a state in which the CL data overlaps the diffuse color texture. FIG. 23F shows the printing result of the transparent color material overlapping, based on the CL data, the image printed based on the RGB data of the diffuse color texture.

Figure 24:
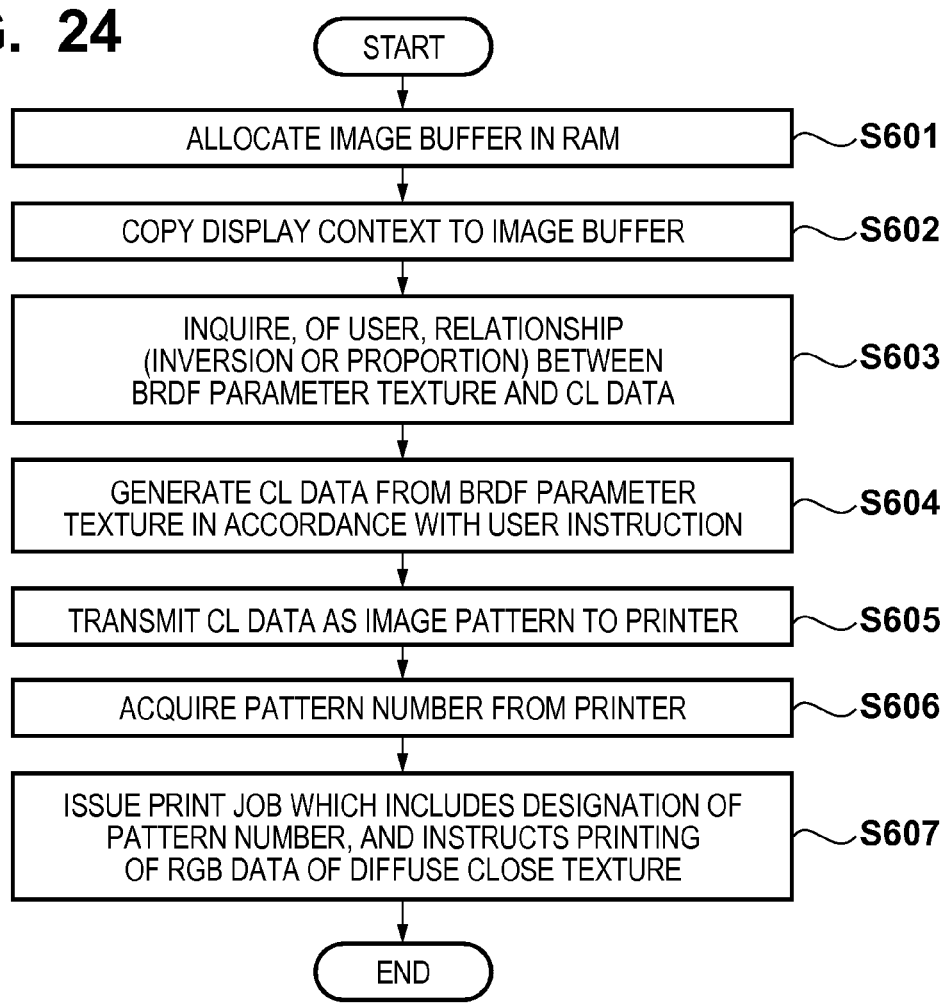
FIG. 24 is a flowchart showing an example of print processing.

An example of print processing will be explained with reference to the flowchart of FIG. 24.

The CPU allocates image buffers (diffuse color texture buffer and BRDF parameter texture buffer) in the RAM of the tablet device 116 (S601). The CPU copies the display contexts (diffuse color texture and BRDF parameter texture) to the image buffers (S602).

The CPU inquires, of the user, the relationship (inversion or proportion) between the BRDF parameter texture and the CL data (S603). The CPU generates CL data from the BRDF parameter texture in accordance with a user instruction (S604), transmits the CL data as an image pattern to the printer (S605), and acquires a pattern number from the printer (S606).

Then, the CPU issues a print job which designates printing of RGB data of the diffuse color texture (S607). The print job designates the pattern number acquired in step S606. In accordance with the print job, the printer prints an image represented by the RGB data, and prints an image pattern corresponding to the pattern number by using the transparent color material to overlap the printed image.

In this way, the appearance of the measurement target object 107 (or reflecting surface) can be reproduced on the screen or printed material by using the BRDF distribution measured from the measurement target object 107 (or reflecting surface).

Modification of Embodiments

When capturing a BRDF distribution, if a directional room illumination or the like exists above the measurement target object 107 (or reflecting surface), specular reflection light of the room illumination may enter the two-dimensional image sensor to generate an error in BRDF measurement. In this case, it suffices to use a light source of the infrared wavelength as the line light source 104, and measure the BRDF distribution at the infrared wavelength hardly contained in the room illumination.

In this case, an optical filter for removing infrared light is not arranged on the two-dimensional image sensor of the camera 101 so that capturing becomes possible in both the visible range and infrared range. Note that all R, G, and B filters arranged in the respective elements of the two-dimensional image sensor transmit infrared light, so a captured image becomes a grayscale image. As an illumination of the visible light wavelength for measuring the diffuse light component, an existing room illumination can be used.

Figure 25:
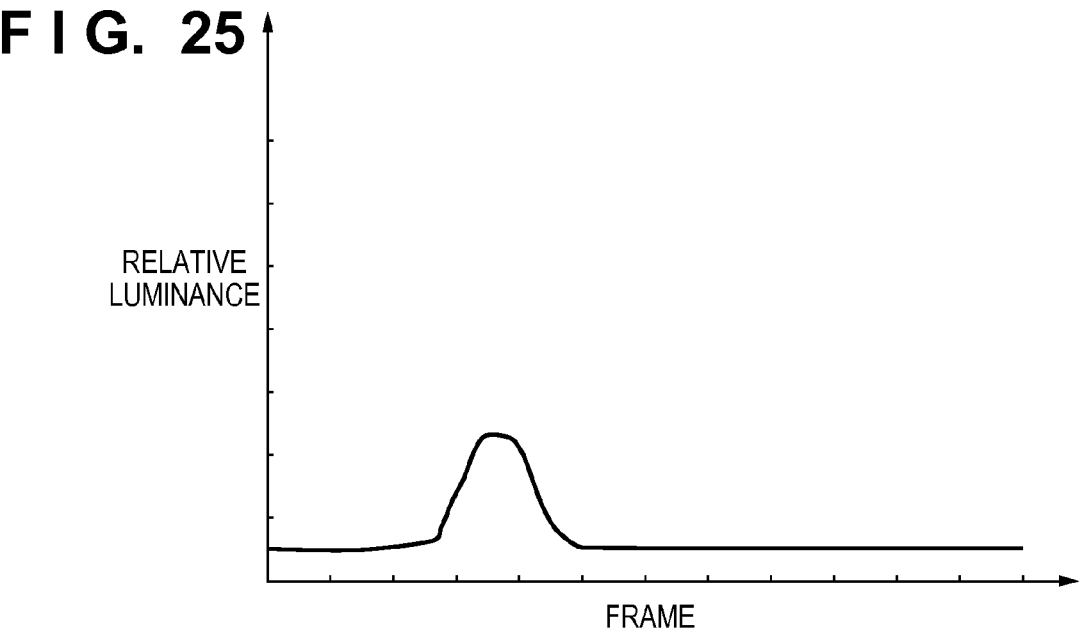
FIG. 25 is a graph showing the result of measuring a BRDF distribution by using infrared light.

FIG. 25 shows the result of measuring a BRDF distribution by using infrared light. A surface roughness distribution (decided by the micro facets coefficient in the Cook-Torrance model) which influences the spread of the specular reflection light component on the reflecting surface hardly influences light in the visible range and infrared range. Therefore, even when infrared light is used, a captured image and a luminance transition (corresponding to each region on the reflecting surface) are obtained, as in the first and second embodiments.

The second embodiment has described the measurement apparatus using the tablet device. However, any computer device including a display and front camera can be similarly used for the measurement apparatus according to the second embodiment. An example of this computer device is a smartphone.

An example in which the display is used as the light source has been described. Alternatively, a light source such as an LED array in which light emitting elements such as light emitting diodes (LEDs) are two-dimensionally arranged as point light sources may be used instead of the display.

Other Embodiment

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-103536 filed May 15, 2013, and Japanese Patent Application No. 2014-083995 filed Apr. 15, 2014, which are hereby incorporated by reference herein in their entirety.

What is claimed is:

1. A measurement system comprising:
a display unit configured to display a moving image based on moving image data;
a capturing unit configured to capture an image of a measurement target object illuminated by the display unit;
a control unit configured to control the display unit and the capturing unit; and
an estimation unit configured to estimate reflection characteristics of the measurement target object from a plurality of images captured by the capturing unit,
wherein the moving image data contains image data representing a line pattern having a plurality of lines arranged in parallel, each line having a predetermined brightness, and
wherein the moving image data is for displaying the moving image representing movement of the plurality of lines in a direction perpendicular to the lines.

2. The measurement system according to claim 1, wherein the control unit provides a user interface configured to input, as a characteristic of the measurement target object, at least one of a size of the measurement target object, a type of the measurement target object, or a visual perception of a material of the measurement target object.

3. The measurement system according to claim 1, wherein the estimation unit estimates a bidirectional reflectance distribution function and a diffuse color as the reflection characteristics from a luminance change of the plurality of images.

4. The measurement system according to claim 1, wherein the control unit controls the display unit to read the moving image data containing image data representing the plurality of lines having an interval set in accordance with a spread amount of a specular reflection light component of the measurement target object based on either of a type of the measurement target object or a visual perception of a material of the measurement target object.

5. The measurement system according to claim 1, wherein the display unit comprises a display screen of a tablet device, and the capturing unit comprises a front camera of the tablet device.

6. The measurement system according to claim 1, wherein the display unit comprises a display screen of a smartphone, and the capturing unit comprises a front camera of the smartphone.

7. The measurement system according to claim 1, wherein the display unit is configured to display an image rendered from the reflection characteristic.

8. The measurement system according to claim 1, further comprising a printing unit configured to cause a printer to print an image rendered from the reflection characteristics.

9. The measurement system according to claim 8, wherein the printing unit generates image data for a transparent color material from a bidirectional reflectance distribution function serving as one of the reflection characteristics to make the transparent color material overlap an image printed based on a diffuse color serving as one of the reflection characteristics.

10. A measurement system comprising:
a display unit configured to display a moving image based on moving image data representing movement of a plurality of ellipses in a two-dimensional space, each ellipse having a predetermined brightness;

a capturing unit configured to capture an image of a measurement target object illuminated by the display unit;
a control unit configured to control the display unit and the capturing unit; and
a calculation unit configured to calculate reflection characteristics of the measurement target object from a plurality of images captured while changing an emission pattern by moving the plurality of ellipses.

11. The measurement system according to claim 10, wherein the control unit controls the display device to read the moving image data that represents a plurality of line patterns or a plurality of elliptic patterns as the emission pattern.

12. The measurement system according to claim 11, wherein the control unit sets an interval between the plurality of line patterns in accordance with a spread amount of a specular reflection light component from the measurement target object based on one of a type of the measurement target object and a visual perception of a material of the measurement target object.

13. The measurement system according to claim 10, wherein the control unit controls change of the emission pattern by moving the plurality of ellipses to not change an aperture angle at which the measurement target object is illuminated.

14. The measurement system according to claim 10, wherein the display unit comprises a display screen of a tablet device, and the capturing unit comprises a front camera of the tablet device.

15. The measurement system according to claim 10, wherein the display unit comprises a display screen of a smartphone, and the capturing unit comprises a front camera of the smartphone.

16. The measurement system according to claim 10, wherein the calculation unit calculates a bidirectional reflectance distribution function and a diffuse color as the reflection characteristics from the change of the emission pattern.

17. The measurement system according to claim 10, further comprising a printing unit configured to cause a printer to print an image rendered from the reflection characteristics.

18. The measurement system according to claim 17, wherein the printing unit generates image data for a transparent color material from a bidirectional reflectance distribution function serving as one of the reflection characteristics to make the transparent color material overlap an image printed based on a diffuse color serving as one of the reflection characteristics.

19. A method for a measurement system having a display unit configured to display a moving image based on moving image data, and a capturing unit configured to capture an image of a measurement target object illuminated by the display unit, the method comprising the steps of:
using a processor to perform the steps of:
controlling the display unit and the capturing unit; and
estimating reflection characteristics of the measurement target object from a plurality of images captured by the capturing unit,
wherein the moving image data is for displaying a line pattern having a plurality of lines arranged in parallel, each line having a predetermined brightness, and
wherein the moving image is displayed based on the moving image data representing movement of the plurality of lines in a direction perpendicular to the lines.

20. A non-transitory computer readable medium storing a computer-executable program executable by a computer to perform a method for a measurement system having a display unit configured to display a moving image based on moving image data, and a capturing unit configured to capture an image of a measurement target object illuminated by the display unit, the method comprising the steps of:
controlling the display unit and the capturing unit; and
estimating reflection characteristics of the measurement target object from a plurality of images captured by the capturing unit,
wherein the moving image data is for displaying a line pattern having a plurality of lines arranged in parallel, each line having a predetermined brightness, and
wherein the moving image is displayed based on the moving image data representing movement of the plurality of lines in a direction perpendicular to the lines.

21. A method for a measurement system having a display unit configured to display a moving image based on moving image data representing movement of a plurality of ellipses in a two-dimensional space, each ellipse having a predetermined brightness, and a capturing unit configured to capture an image of a measurement target object illuminated by the display unit, the method comprising the steps of:
using a processor to perform the steps of:
controlling the display unit and the capturing unit; and
calculating reflection characteristics of the measurement target object from a plurality of images captured while changing an emission pattern by moving the plurality of ellipses.

22. A non-transitory computer readable medium storing a computer-executable program executable by a computer to perform a method for a measurement system having a display unit configured to display a moving image based on moving image data representing movement of a plurality of ellipses in a two-dimensional space, each ellipse having a predetermined brightness, and a capturing unit configured to capture an image of a measurement target object illuminated by the display device, the method comprising the steps of:
controlling the display unit and the capturing unit; and
calculating reflection characteristics of the measurement target object from a plurality of images captured while changing the emission pattern by moving the plurality of ellipses.

23. A measurement system comprising:
a display unit configured to display a moving image based on moving image data;
a capturing unit configured to capture an image of an object; and
a control unit configured to, in a case where reflection characteristics of an object is obtained:
supply moving image data, which contains image data representing a line pattern having a plurality of lines arranged in parallel, each line having a predetermined brightness, to the display unit to display the moving image representing movement of the plurality of lines in a direction perpendicular to the lines; and
control the capturing unit to capture a plurality of images of the object illuminated by the display unit.

24. A method for a measurement system having a display unit configured to display a moving image based on moving image data, and a capturing unit configured to capture an image of an object, the method comprising the steps of:
using, in a case where reflection characteristics of an object is obtained, a processor to perform steps of:
supplying moving image data, which contains image data representing a line pattern having a plurality of lines arranged in parallel, each line having a predetermined brightness, to the display unit to display the moving image representing movement of the plurality of lines in a direction perpendicular to the lines; and capturing a plurality of images of the object illuminated by the display unit using the capturing unit.

\* \* \* \* \*